US011077143B2

(12) United States Patent
Klingemann et al.

(10) Patent No.: US 11,077,143 B2
(45) Date of Patent: Aug. 3, 2021

(54) ELIMINATION OF PD-L1-POSITIVE MALIGNANCIES BY PD-L1 CHIMERIC ANTIGEN RECEPTOR-EXPRESSING NK CELLS

(71) Applicant: NANTKWEST, INC., San Diego, CA (US)

(72) Inventors: Hans G. Klingemann, San Diego, CA (US); Laurent H. Boissel, San Diego, CA (US); Abhijit Dandapat, San Diego, CA (US)

(73) Assignee: NantKwest Inc., San Diego, CA (US)

( * ) Notice: Subject to any disclaimer, the term of this patent is extended or adjusted under 35 U.S.C. 154(b) by 0 days.

(21) Appl. No.: 16/529,159

(22) Filed: Aug. 1, 2019

(65) Prior Publication Data
US 2020/0129552 A1 Apr. 30, 2020

Related U.S. Application Data

(60) Provisional application No. 62/753,740, filed on Oct. 31, 2018.

(51) Int. Cl.
| A61K 35/17 | (2015.01) |
| A61P 35/00 | (2006.01) |
| C07K 14/735 | (2006.01) |
| C07K 14/725 | (2006.01) |
| A61P 35/04 | (2006.01) |
| C07K 14/54 | (2006.01) |
| C07K 16/28 | (2006.01) |
| C07K 14/55 | (2006.01) |

(52) U.S. Cl.
CPC .............. A61K 35/17 (2013.01); A61P 35/04 (2018.01); C07K 14/5443 (2013.01); C07K 14/55 (2013.01); C07K 14/7051 (2013.01); C07K 14/70535 (2013.01); C07K 16/2827 (2013.01)

(58) Field of Classification Search
None
See application file for complete search history.

(56) References Cited

U.S. PATENT DOCUMENTS

| 2013/0040386 A1 | 2/2013 | Campbell |
| 2018/0002424 A1 | 1/2018 | Belk et al. |
| 2018/0187149 A1* | 7/2018 | Ma ................... C07K 14/70578 |
| 2018/0193383 A1* | 7/2018 | Lee ................... C07K 16/2827 |

FOREIGN PATENT DOCUMENTS

| CN | 112567024 A | | 3/2021 |
| WO | 2017100709 A1 | | 6/2017 |
| WO | 2018013975 A1 | | 1/2018 |
| WO | WO2018/075989 | * | 1/2018 |
| WO | WO 2019/152513 | * | 8/2019 |
| WO | WO 2019226708 | * | 11/2019 |

OTHER PUBLICATIONS

Boyerinas, B. et al. Antibody dependent cellular cytotoxicity activity of a novel anti-PD-L1 antibody, avelumab (MSB0010718C), on human tumor cells Cancer Immunol. Res. 3, 1148-1157.*
Hodson, J., Internet webpage, NantKwest, "NantKwest Launches First-in-Class, First-in-Human Phase I Clinical Trial with a Targeted PD-L1 t-haNK Cell Therapy in Patients with Solid Tumors", URL: "https://nantkwest.com/nantkwest-launches-first-in-class-first-in-human-phase-i-clinical-trialwith-a-targeted-pd-l1-t-hank-cell-therapy-in-patients-with-solid-tumors/", 6 pages.
International Search Report and Written Opinion Received for PCT Application Serial No. PCT/US2019/044637 dated Nov. 29, 2019, 13 Pages.
Jochems, C. et al., "ADCC employing an NK cell line (haNK) expressing the high affinity CD16 allele with avelumab, an anti-PD-L1 antibody", International journal of cancer, 2017, vol. 141, pp. 583-593.
Morvan, M. G. et al., "NK cells and cancer: you can teach innate cells new tricks", Nature Reviews Cancer, 2016, vol. 16, pp. 7-19.
International Preliminary Report on Patentability Chapter I received for PCT International Application No. PCT/US2019/044637 dated May 14, 2021, 8 Pages.

* cited by examiner

Primary Examiner — Maria G Leavitt
(74) Attorney, Agent, or Firm — Martin Fessenmaier; Umberg Zipser LLP

(57) ABSTRACT

Provided herein are compositions of NK-92™ cells that express a combination of PD-L1 CAR, CD16 and IL2, and the method of using these cells to reduce tumor cells and cells in tumor microenvironment (e.g., MDSCs or TAMs) and treat cancer.

9 Claims, 15 Drawing Sheets

Specification includes a Sequence Listing.

SEQUENCE LISTING

<160> NUMBER OF SEQ ID NOS: 15

<210> SEQ ID NO 1
<211> LENGTH: 236
<212> TYPE: PRT
<213> ORGANISM: Homo sapiens -continued
<220> FEATURE:
<221> NAME/KEY: misc_feature
<223> OTHER INFORMATION: Low Affinity Immunoglobulin Gamma Fc Region
      Receptor III-A amino acid sequence (mature form)

<400> SEQUENCE: 1

Arg Thr Glu Asp Leu Pro Lys Ala Val Val Phe Leu Glu Pro Gln Trp
1               5                   10                  15

Tyr Arg Val Leu Glu Lys Asp Ser Val Thr Leu Lys Cys Gln Gly Ala
            20                  25                  30

Tyr Ser Pro Glu Asp Asn Ser Thr Gln Trp Phe His Asn Glu Ser Leu
        35                  40                  45

Ile Ser Ser Gln Ala Ser Ser Tyr Phe Ile Asp Ala Ala Thr Val Asp
50                  55                  60

Asp Ser Gly Glu Tyr Arg Cys Gln Thr Asn Leu Ser Thr Leu Ser Asp
65                  70                  75                  80

Pro Val Gln Leu Glu Val His Ile Gly Trp Leu Leu Leu Gln Ala Pro
                85                  90                  95

Arg Trp Val Phe Lys Glu Glu Asp Pro Ile His Leu Arg Cys His Ser
            100                 105                 110

Trp Lys Asn Thr Ala Leu His Lys Val Thr Tyr Leu Gln Asn Gly Lys
        115                 120                 125

Gly Arg Lys Tyr Phe His His Asn Ser Asp Phe Tyr Ile Pro Lys Ala
130                 135                 140

Thr Leu Lys Asp Ser Gly Ser Tyr Phe Cys Arg Gly Leu Phe Gly Ser
145                 150                 155                 160

Lys Asn Val Ser Ser Glu Thr Val Asn Ile Thr Ile Thr Gln Gly Leu
                165                 170                 175

Ala Val Ser Thr Ile Ser Ser Phe Phe Pro Pro Gly Tyr Gln Val Ser
            180                 185                 190

Phe Cys Leu Val Met Val Leu Leu Phe Ala Val Asp Thr Gly Leu Tyr
        195                 200                 205

Phe Ser Val Lys Thr Asn Ile Arg Ser Ser Thr Arg Asp Trp Lys Asp
210                 215                 220

His Lys Phe Lys Trp Arg Lys Asp Pro Gln Asp Lys
225                 230                 235

<210> SEQ ID NO 2
<211> LENGTH: 236
<212> TYPE: PRT
<213> ORGANISM: Homo sapiens
<220> FEATURE:
<221> NAME/KEY: misc_feature
<223> OTHER INFORMATION: High Affinity Variant F158V Immunoglobulin
      Gamma Fc Region Receptor III-A amino acid sequence (mature form)

<400> SEQUENCE: 2

Arg Thr Glu Asp Leu Pro Lys Ala Val Val Phe Leu Glu Pro Gln Trp
1               5                   10                  15

Tyr Arg Val Leu Glu Lys Asp Ser Val Thr Leu Lys Cys Gln Gly Ala
            20                  25                  30

Tyr Ser Pro Glu Asp Asn Ser Thr Gln Trp Phe His Asn Glu Ser Leu
        35                  40                  45

Ile Ser Ser Gln Ala Ser Ser Tyr Phe Ile Asp Ala Ala Thr Val Asp
50                  55                  60

Asp Ser Gly Glu Tyr Arg Cys Gln Thr Asn Leu Ser Thr Leu Ser Asp
65                  70                  75                  80

```
Pro Val Gln Leu Glu Val His Ile Gly Trp Leu Leu Leu Gln Ala Pro
                85                  90                  95

Arg Trp Val Phe Lys Glu Glu Asp Pro Ile His Leu Arg Cys His Ser
            100                 105                 110

Trp Lys Asn Thr Ala Leu His Lys Val Thr Tyr Leu Gln Asn Gly Lys
        115                 120                 125

Gly Arg Lys Tyr Phe His His Asn Ser Asp Phe Tyr Ile Pro Lys Ala
    130                 135                 140

Thr Leu Lys Asp Ser Gly Ser Tyr Phe Cys Arg Gly Leu Val Gly Ser
145                 150                 155                 160

Lys Asn Val Ser Ser Glu Thr Val Asn Ile Thr Ile Thr Gln Gly Leu
                165                 170                 175

Ala Val Ser Thr Ile Ser Ser Phe Phe Pro Pro Gly Tyr Gln Val Ser
            180                 185                 190

Phe Cys Leu Val Met Val Leu Leu Phe Ala Val Asp Thr Gly Leu Tyr
        195                 200                 205

Phe Ser Val Lys Thr Asn Ile Arg Ser Ser Thr Arg Asp Trp Lys Asp
    210                 215                 220

His Lys Phe Lys Trp Arg Lys Asp Pro Gln Asp Lys
225                 230                 235

<210> SEQ ID NO 3
<211> LENGTH: 254
<212> TYPE: PRT
<213> ORGANISM: Homo sapiens
<220> FEATURE:
<221> NAME/KEY: misc_feature
<223> OTHER INFORMATION: Low Affinity Immunoglobulin Gamma Fc Region
      Receptor III-A amino acid sequence (precursor form)

<400> SEQUENCE: 3

Met Trp Gln Leu Leu Leu Pro Thr Ala Leu Leu Leu Leu Val Ser Ala
1               5                   10                  15

Gly Met Arg Thr Glu Asp Leu Pro Lys Ala Val Val Phe Leu Glu Pro
            20                  25                  30

Gln Trp Tyr Arg Val Leu Glu Lys Asp Ser Val Thr Leu Lys Cys Gln
        35                  40                  45

Gly Ala Tyr Ser Pro Glu Asp Asn Ser Thr Gln Trp Phe His Asn Glu
    50                  55                  60

Ser Leu Ile Ser Ser Gln Ala Ser Ser Tyr Phe Ile Asp Ala Ala Thr
65                  70                  75                  80

Val Asp Asp Ser Gly Glu Tyr Arg Cys Gln Thr Asn Leu Ser Thr Leu
                85                  90                  95

Ser Asp Pro Val Gln Leu Glu Val His Ile Gly Trp Leu Leu Leu Gln
            100                 105                 110

Ala Pro Arg Trp Val Phe Lys Glu Glu Asp Pro Ile His Leu Arg Cys
        115                 120                 125

His Ser Trp Lys Asn Thr Ala Leu His Lys Val Thr Tyr Leu Gln Asn
    130                 135                 140

Gly Lys Gly Arg Lys Tyr Phe His His Asn Ser Asp Phe Tyr Ile Pro
145                 150                 155                 160

Lys Ala Thr Leu Lys Asp Ser Gly Ser Tyr Phe Cys Arg Gly Leu Phe
                165                 170                 175

Gly Ser Lys Asn Val Ser Ser Glu Thr Val Asn Ile Thr Ile Thr Gln
            180                 185                 190
```

```
Gly Leu Ala Val Ser Thr Ile Ser Ser Phe Phe Pro Pro Gly Tyr Gln
            195                 200                 205

Val Ser Phe Cys Leu Val Met Val Leu Leu Phe Ala Val Asp Thr Gly
    210                 215                 220

Leu Tyr Phe Ser Val Lys Thr Asn Ile Arg Ser Ser Thr Arg Asp Trp
225                 230                 235                 240

Lys Asp His Lys Phe Lys Trp Arg Lys Asp Pro Gln Asp Lys
                245                 250

<210> SEQ ID NO 4
<211> LENGTH: 254
<212> TYPE: PRT
<213> ORGANISM: Homo sapiens
<220> FEATURE:
<221> NAME/KEY: misc_feature
<223> OTHER INFORMATION: High Affinity Variant Immunoglobulin Gamma Fc
      Region Receptor III-A amino acid sequence (precursor form)

<400> SEQUENCE: 4

Met Trp Gln Leu Leu Pro Thr Ala Leu Leu Leu Leu Val Ser Ala
1               5                   10                  15

Gly Met Arg Thr Glu Asp Leu Pro Lys Ala Val Val Phe Leu Glu Pro
            20                  25                  30

Gln Trp Tyr Arg Val Leu Glu Lys Asp Ser Val Thr Leu Lys Cys Gln
        35                  40                  45

Gly Ala Tyr Ser Pro Glu Asp Asn Ser Thr Gln Trp Phe His Asn Glu
    50                  55                  60

Ser Leu Ile Ser Ser Gln Ala Ser Ser Tyr Phe Ile Asp Ala Ala Thr
65                  70                  75                  80

Val Asp Asp Ser Gly Glu Tyr Arg Cys Gln Thr Asn Leu Ser Thr Leu
                85                  90                  95

Ser Asp Pro Val Gln Leu Glu Val His Ile Gly Trp Leu Leu Leu Gln
            100                 105                 110

Ala Pro Arg Trp Val Phe Lys Glu Glu Asp Pro Ile His Leu Arg Cys
        115                 120                 125

His Ser Trp Lys Asn Thr Ala Leu His Lys Val Thr Tyr Leu Gln Asn
    130                 135                 140

Gly Lys Gly Arg Lys Tyr Phe His His Asn Ser Asp Phe Tyr Ile Pro
145                 150                 155                 160

Lys Ala Thr Leu Lys Asp Ser Gly Ser Tyr Phe Cys Arg Gly Leu Val
                165                 170                 175

Gly Ser Lys Asn Val Ser Ser Glu Thr Val Asn Ile Thr Ile Thr Gln
            180                 185                 190

Gly Leu Ala Val Ser Thr Ile Ser Ser Phe Phe Pro Pro Gly Tyr Gln
        195                 200                 205

Val Ser Phe Cys Leu Val Met Val Leu Leu Phe Ala Val Asp Thr Gly
    210                 215                 220

Leu Tyr Phe Ser Val Lys Thr Asn Ile Arg Ser Ser Thr Arg Asp Trp
225                 230                 235                 240

Lys Asp His Lys Phe Lys Trp Arg Lys Asp Pro Gln Asp Lys
                245                 250

<210> SEQ ID NO 5
<211> LENGTH: 765
<212> TYPE: DNA
<213> ORGANISM: Homo sapiens
```

```
<220> FEATURE:
<221> NAME/KEY: misc_feature
<223> OTHER INFORMATION: Polynucleotide Encoding the Low Affinity
      Immunoglobulin Gamma Fc Region Receptor III-A (Precursor)

<400> SEQUENCE: 5
atgtggcagc tgctcctccc aactgctctg ctacttctag tttcagctgg catgcggact     60
gaagatctcc caaaggctgt ggtgttcctg agcctcaat ggtacagggt gctcgagaag     120
gacagtgtga ctctgaagtg ccagggagcc tactcccctg aggacaattc cacacagtgg    180
tttcacaatg agagcctcat ctcaagccag gcctcgagct acttcattga cgctgccaca   240
gtcgacgaca gtggagagta caggtgccag acaaacctct ccaccctcag tgacccggtg   300
cagctagaag tccatatcgg ctggctgttg ctccaggccc ctcggtgggt gttcaaggag   360
gaagacccta ttcacctgag gtgtcacagc tggaagaaca ctgctctgca taaggtcaca   420
tatttacaga tggcaaagg caggaagtat tttcatcata attctgactt ctacattcca   480
aaagccacac tcaaagacag cggctcctac ttctgcaggg ggcttttgg gagtaaaaat    540 gtgtcttcag agactgtgaa catcaccatc actcaaggtt tggcagtgtc aaccatctca   600
tcattctttc cacctgggta ccaagtctct ttctgcttgg tgatggtact ccttttgca    660 gtggacacag gactatattt ctctgtgaag acaaacattc gaagctcaac aagagactgg   720
aaggaccata atttaaatg gagaaaggac cctcaagaca atga                     765

<210> SEQ ID NO 6
<211> LENGTH: 153
<212> TYPE: PRT
<213> ORGANISM: Homo sapiens
<220> FEATURE:
<221> NAME/KEY: misc_feature
<223> OTHER INFORMATION: Wild-Type IL-2

<400> SEQUENCE: 6

Met Tyr Arg Met Gln Leu Leu Ser Cys Ile Ala Leu Ser Leu Ala Leu
1               5                   10                  15

Val Thr Asn Ser Ala Pro Thr Ser Ser Ser Thr Lys Lys Thr Gln Leu
                20                  25                  30

Gln Leu Glu His Leu Leu Leu Asp Leu Gln Met Ile Leu Asn Gly Ile
            35                  40                  45

Asn Asn Tyr Lys Asn Pro Lys Leu Thr Arg Met Leu Thr Phe Lys Phe
        50                  55                  60

Tyr Met Pro Lys Lys Ala Thr Glu Leu Lys His Leu Gln Cys Leu Glu
65                  70                  75                  80

Glu Glu Leu Lys Pro Leu Glu Glu Val Leu Asn Leu Ala Gln Ser Lys
                85                  90                  95

Asn Phe His Leu Arg Pro Arg Asp Leu Ile Ser Asn Ile Asn Val Ile
            100                 105                 110

Val Leu Glu Leu Lys Gly Ser Glu Thr Thr Phe Met Cys Glu Tyr Ala
        115                 120                 125

Asp Glu Thr Ala Thr Ile Val Glu Phe Leu Asn Arg Trp Ile Thr Phe
    130                 135                 140

Cys Gln Ser Ile Ile Ser Thr Leu Thr
145                 150

<210> SEQ ID NO 7
<211> LENGTH: 160
<212> TYPE: PRT
<213> ORGANISM: Homo sapiens
```

```
<220> FEATURE:
<221> NAME/KEY: misc_feature
<223> OTHER INFORMATION: er-IL2

<400> SEQUENCE: 7

Met Tyr Arg Met Gln Leu Leu Ser Cys Ile Ala Leu Ser Leu Ala Leu
1               5                   10                  15

Val Thr Asn Ser Ala Pro Thr Ser Ser Ser Thr Lys Lys Thr Gln Leu
            20                  25                  30

Gln Leu Glu His Leu Leu Leu Asp Leu Gln Met Ile Leu Asn Gly Ile
        35                  40                  45

Asn Asn Tyr Lys Asn Pro Lys Leu Thr Arg Met Leu Thr Phe Lys Phe
50                  55                  60

Tyr Met Pro Lys Lys Ala Thr Glu Leu Lys His Leu Gln Cys Leu Glu
65                  70                  75                  80

Glu Glu Leu Lys Pro Leu Glu Glu Val Leu Asn Leu Ala Gln Ser Lys
                85                  90                  95

Asn Phe His Leu Arg Pro Arg Asp Leu Ile Ser Asn Ile Asn Val Ile
            100                 105                 110

Val Leu Glu Leu Lys Gly Ser Glu Thr Thr Phe Met Cys Glu Tyr Ala
        115                 120                 125

Asp Glu Thr Ala Thr Ile Val Glu Phe Leu Asn Arg Trp Ile Thr Phe
    130                 135                 140

Cys Gln Ser Ile Ile Ser Thr Leu Thr Gly Ser Glu Lys Asp Glu Leu
145                 150                 155                 160

<210> SEQ ID NO 8
<211> LENGTH: 66
<212> TYPE: DNA
<213> ORGANISM: Artificial Sequence
<220> FEATURE:
<223> OTHER INFORMATION: Artificial P2A sequence
<220> FEATURE:
<221> NAME/KEY: misc_feature
<223> OTHER INFORMATION: P2A sequence

<400> SEQUENCE: 8
ggaagcggag ctactaactt cagcctgctg aagcaggctg agacgtgga ggagaaccct      60 ggacct                                                               66

<210> SEQ ID NO 9
<211> LENGTH: 807
<212> TYPE: DNA
<213> ORGANISM: Artificial Sequence
<220> FEATURE:
<223> OTHER INFORMATION: Artificial codon optimized PD-L1 scFv sequence

<400> SEQUENCE: 9
atggactgga tctggcggat tctgtttctc gtgggagctg ccacaggcgc tcattctgct      60
cagcctgcca acatccagat gacccagtct ccatcttctg tgtctgcatc tgtaggagac     120
agagtcacca tcacttgtcg ggcgagtcag gatattagcc gctggttagc ctggtatcag     180
cagaaaccag ggaaagcccc taaactcctg atctatgctg catccagttt gcaaagtggg     240
gtcccatcga ggttcagcgg cagtggatct gggacagatt tcgctctcac tatcagcagc     300
ctgcagcctg aagattttgc aacttactat tgtcaacagg ctgacagtcg tttctcgatc     360
accttcggcc aagggacacg actggagatt aaaggcggcg aggaagcgg aggcggagga     420 tctgggggcg gaggctctgg cggaggggga tctgaggtgc agctggtgca gtctggggga     480
```

```
ggcttggtac agcctggggg gtccctgaga ctctcctgtg cagcctctgg attcaccttc    540
agtagctata gcatgaactg ggtccgccag gctccaggga aggggctgga gtgggtttca    600
tacattagta gtagtagtag taccatacag tacgcagact ctgtgaaggg ccgattcacc    660
atctccagag acaatgccaa gaactcactg tatctgcaaa tgaacagcct gagagacgag    720
gacacggctg tgtattactg tgcgagaggg gactactact acggtatgga cgtctggggc    780
caagggacca cggtcaccgt gagctca                                        807
```

<210> SEQ ID NO 10
<211> LENGTH: 269
<212> TYPE: PRT
<213> ORGANISM: Artificial Sequence
<220> FEATURE:
<223> OTHER INFORMATION: Artificial PD-L1 scFv sequence

<400> SEQUENCE: 10

```
Met Asp Trp Ile Trp Arg Ile Leu Phe Leu Val Gly Ala Ala Thr Gly
 1               5                  10                  15

Ala His Ser Ala Gln Pro Ala Asn Ile Gln Met Thr Gln Ser Pro Ser
             20                  25                  30

Ser Val Ser Ala Ser Val Gly Asp Arg Val Thr Ile Thr Cys Arg Ala
         35                  40                  45

Ser Gln Asp Ile Ser Arg Trp Leu Ala Trp Tyr Gln Gln Lys Pro Gly
     50                  55                  60

Lys Ala Pro Lys Leu Leu Ile Tyr Ala Ala Ser Ser Leu Gln Ser Gly
 65                  70                  75                  80

Val Pro Ser Arg Phe Ser Gly Ser Gly Ser Gly Thr Asp Phe Ala Leu
                 85                  90                  95

Thr Ile Ser Ser Leu Gln Pro Glu Asp Phe Ala Thr Tyr Tyr Cys Gln
            100                 105                 110

Gln Ala Asp Ser Arg Phe Ser Ile Thr Phe Gly Gln Gly Thr Arg Leu
        115                 120                 125

Glu Ile Lys Gly Gly Gly Gly Ser Gly Gly Gly Gly Ser Gly Gly Gly
    130                 135                 140

Gly Ser Gly Gly Gly Gly Ser Glu Val Gln Leu Val Gln Ser Gly Gly
145                 150                 155                 160

Gly Leu Val Gln Pro Gly Gly Ser Leu Arg Leu Ser Cys Ala Ala Ser
                165                 170                 175

Gly Phe Thr Phe Ser Ser Tyr Ser Met Asn Trp Val Arg Gln Ala Pro
            180                 185                 190

Gly Lys Gly Leu Glu Trp Val Ser Tyr Ile Ser Ser Ser Ser Thr
        195                 200                 205

Ile Gln Tyr Ala Asp Ser Val Lys Gly Arg Phe Thr Ile Ser Arg Asp
    210                 215                 220

Asn Ala Lys Asn Ser Leu Tyr Leu Gln Met Asn Ser Leu Arg Asp Glu
225                 230                 235                 240

Asp Thr Ala Val Tyr Tyr Cys Ala Arg Gly Asp Tyr Tyr Tyr Gly Met
                245                 250                 255

Asp Val Trp Gly Gln Gly Thr Thr Val Thr Val Ser Ser
            260                 265
```

<210> SEQ ID NO 11
<211> LENGTH: 6772
<212> TYPE: DNA
<213> ORGANISM: Artificial Sequence

```
<220> FEATURE:
<223> OTHER INFORMATION: Artificial tricistronic construct encoding
      PD-L1 CAR, CD16, and erIL-2
<220> FEATURE:
<221> NAME/KEY: anti PD-L1 scFv sequence
<222> LOCATION: (1552)..(2358)
<220> FEATURE:
<221> NAME/KEY: CD8 hinge
<222> LOCATION: (2367)..(2559)
<220> FEATURE:
<221> NAME/KEY: CD28 transmembrane
<222> LOCATION: (2560)..(2635)
<220> FEATURE:
<221> NAME/KEY: FceRIg signaling domain
<222> LOCATION: (2636)..(2766)
<220> FEATURE:
<221> NAME/KEY: P2A sequence
<222> LOCATION: (2767)..(2832)
<220> FEATURE:
<221> NAME/KEY: CD16 sequence
<222> LOCATION: (2833)..(3597)
<220> FEATURE:
<221> NAME/KEY: ERIL-2 sequence
<222> LOCATION: (4199)..(4681)

<400> SEQUENCE: 11
tgtatttaga aaataaaca aataggggtt ccgcgcacat tccccgaaa agtgccacct    60 gacgtcgacg gatcgggaga tctcccgatc ccctatggtg cactctcagt acaatctgct   120
ctgatgccgc atagttaagc cagtatctgc tccctgcttg tgtgttggag gtcgctgagt   180
agtgcgcgag caaaatttaa gctacaacaa ggcaaggctt gaccgacaat gcatgaaga   240 atctgcttag ggttaggcgt tttgcgctgc ttcgggatcc gctgaccaaa agagcaccaa   300
aggcgccctg accttcagcc cctacctgcg ctccggtgcc cgtcagtggg cagagcgcac   360
atcgcccaca gtccccgaga gttgggggg aggggtcggc aattgaaccg gtgcctagag   420
aaggtggcgc ggggtaaact gggaaagtga tgtcgtgtac tggctccgcc ttttttcccga   480 gggtggggga gaaccgtata taagtgcagt agtcgccgtg aacgttcttt ttcgcaacgg   540
gtttgccgcc agaacacagg taagtgccgt gtgtggttcc cgcgggcctg gcctctttac   600
gggttatggc ccttgcgtgc cttgaattac ttccacctgg ctgcagtacg tgattcttga   660
tcccgagctt cgggttggaa gtgggtggga gagttcgagg ccttgcgctt aaggagcccc   720
ttcgcctcgt gcttgagttg aggcctggcc tgggcgctgg ggccgccgcg tgcgaatctg   780
gtggcaccct cgcgcctgtc tcgctgcttt cgataagtct ctagccattt aaaatttttg   840
atgacctgct gcgacgcttt ttttctggca agatagtct gtaaatgcgg gccaagatct   900
gcacactggt atttcggttt tggggccgc gggcggcgac ggggcccgtg cgtcccagcg   960
cacatgttcg gcgaggcggg gcctgcgagc gcggccaccg agaatcggac gggggtagtc  1020
tcaagctggc cggcctgctc tggtgcctgg cctcgcgccg ccgtgtatcg ccccgccctg  1080
ggcggcaagg ctggcccggt cggcaccagt tgcgtgagcg gaaagatggc cgcttcccgg  1140
ccctgctgca gggagctcaa aatggaggac gcggcgctcg ggagagcggg cggtgagtc   1200 acccacacaa aggaaaaggg cctttccgtc ctcagccgtc gcttcatgtg actccacgga  1260
gtaccgggcg ccgtccaggc acctcgatta gttctcgagc ttttggagta cgtcgtcttt  1320
aggttggggg gaggggtttt atgcgatgga gtttccccac actgagtggg tggagactga  1380
agttaggcca gcttggcact tgatgtaatt ctccttggaa tttgccctt ttgagtttgg  1440 atcttggttc attctcaagc ctcagacagt ggttcaaagt ttttttcttc catttcaggt  1500
gtcgtgataa tacgactcac tatagggaga cccaagctgg aattcgccac catggactgg  1560
```

```
atctggcgga ttctgtttct cgtgggagct gccacaggcg ctcattctgc tcagcctgcc    1620
aacatccaga tgacccagtc tccatcttct gtgtctgcat ctgtaggaga cagagtcacc    1680
atcacttgtc gggcgagtca ggatattagc cgctggttag cctggtatca gcagaaacca    1740
gggaaagccc ctaaactcct gatctatgct gcatccagtt tgcaaagtgg ggtcccatcg    1800
aggttcagcg gcagtggatc tgggacagat ttcgctctca ctatcagcag cctgcagcct    1860
gaagattttg caacttacta ttgtcaacag gctgacagtc gttttctcga caccttcggc    1920
caagggacac gactggagat taaaggcggc ggaggaagcg gaggcggagg atctgggggc    1980
ggaggctctg gcggaggggg atctgaggtg cagctggtgc agtctggggg aggcttggta    2040
cagcctgggg ggtccctgag actctcctgt gcagcctctg gattcacctt cagtagctat    2100
agcatgaact gggtccgcca ggctccaggg aaggggctgg agtgggtttc atacattagt    2160
agtagtagta gtaccataca gtacgcagac tctgtgaagg gccgattcac catctccaga    2220
gacaatgcca agaactcact gtatctgcaa atgaacagcc tgagagacga ggacacggct    2280
gtgtattact gtgcgagagg ggactactac tacggtatgg acgtctgggg ccaagggacc    2340
acggtcaccg tgagctcagc ggccgcgctg agcaacagca tcatgtactt cagccacttc    2400
gtgcctgtgt tcctgcctgc caagcctaca acaaccagcc ccctagacc tccaacccct    2460
gcccctacaa ttgcctctca gcctctgtct ctgaggcccg aagcttgtag acctgctgct    2520
ggcggagctg tgcacaccag aggactggat ttcgcctgct tttgggtgct ggtggtcgtg    2580
ggcggagtgc tggcttgtta ttctctgctg gtcaccgtgg ccttcatcat cttttgggtc    2640
cgactgaaga tccaggtccg aaaggccgcc atcaccagct acgagaagtc tgatggcgtg    2700
tacaccggcc tgagcaccag aaaccaggaa acctacgaga cactgaagca cgagaagccc    2760
ccccaggga t ctggagctac taacttcagc ctgctgaagc aggctggaga cgtggaggag    2820
aaccctggac ctatgtggca gctgctgctg cctacagctc tcctgctgct ggtgtccgcc    2880
ggcatgagaa ccgaggatct gcctaaggcc gtggtgttcc tggaacccca gtggtacaga    2940
gtgctggaaa aggacagcgt gaccctgaag tgccagggcg cctacagccc cgaggacaat    3000
agcacccagt ggttccacaa cgagagcctg atcagcagcc aggccagcag ctacttcatc    3060
gacgccgcca ccgtggacga cagcggcgag tatagatgcc agaccaacct gagcaccctg    3120
agcgaccccg tgcagctgga agtgcacatc ggatggctgc tgctgcaggc ccccagatgg    3180
gtgttcaaag aagaggaccc catccacctg agatgccact cttggaagaa caccgccctg    3240
cacaaagtga cctacctgca gaacggcaag gcagaaagt acttccacca acagcgac    3300
ttctacatcc ccaaggccac cctgaaggac tccggctcct acttctgcag aggcctcgtg    3360
ggcagcaaga acgtgtccag cgagacagtg aacatcacca tcacccaggg cctggccgtg    3420
tctaccatca gcagcttttt cccacccggc taccaggtgt ccttctgcct cgtgatggtg    3480
ctgctgttcg ccgtggacac cggcctgtac ttcagcgtga aaacaaacat cagaagcagc    3540
acccgggact ggaaggacca caagttcaag tggcggaagg accccagga caagtgaaat    3600
tccgcccctc tccccccccc ccctctccct cccccccccc taacgttact ggccgaagcc    3660
gcttggaata aggccggtgt gcgtttgtct atatgttatt ttccaccata ttgccgtctt    3720
ttggcaatgt gagggcccgg aaacctggcc ctgtcttctt gacgagcatt cctagggtc    3780
tttccctct cgccaaagga atgcaaggtc tgttgaatgt cgtgaaggaa gcagttcctc    3840
tggaagcttc ttgaagacaa acaacgtctg tagcgaccct ttgcaggcag cggaacccc    3900
cacctggcga caggtgcctc tgcggccaaa agccacgtgt ataagataca cctgcaaagg    3960
```

```
cggcacaacc ccagtgccac gttgtgagtt ggatagttgt ggaaagagtc aaatggctct    4020
cctcaagcgt attcaacaag gggctgaagg atgcccagaa ggtacccccat tgtatgggat    4080 ctgatctggg gcctcggtgc acatgcttta catgtgttta gtcgaggtta aaaaaacgtc    4140
taggcccccc gaaccacggg gacgtggttt tcctttgaaa aacacgataa ccgccaccat    4200
gtaccggatg cagctgctga gctgtatcgc cctgtctctg gccctcgtga ccaacagcgc    4260
ccctaccagc agcagcacca agaaaaccca gctgcagctg aacatctgc tgctggacct    4320 gcagatgatc ctgaacggca tcaacaacta caagaacccc aagctgaccc ggatgctgac    4380
cttcaagttc tacatgccca agaaggccac cgaactgaaa catctgcagt gcctggaaga    4440
ggaactgaag cccctggaag aagtgctgaa cctggcccag agcaagaact tccacctgag    4500
gcccagggac ctgatcagca acatcaacgt gatcgtgctg gaactgaaag gcagcgagac    4560
aaccttcatg tgcgagtacg ccgacgagac agctaccatc gtggaatttc tgaaccggtg    4620
gatcaccttc tgccagagca tcatcagcac cctgaccggc tccgagaagg acgagctgtg    4680
agcggccgcc cgctgatcag cctcgaacga gatttcgatt ccaccgccgc cttctatgaa    4740
aggttgggct tcggaatcgt tttccgggac gccggctgga tgatcctcca gcgcggggat    4800
ctcatgctgg agttcttcgc ccaccccaac ttgtttattg cagcttataa tggttacaaa    4860
taaagcaata gcatcacaaa tttcacaaat aaagcatttt tttcactgca ttctagttgt    4920
ggtttgtcca aactcatcaa tgtatcttat catgtctgtg cggtgggctc tatggcttct    4980
gaggcggaaa gaaccagctg gggctctagg gggtatcccc ggatcctgag caaaaggcca    5040
gcaaaaggcc aggaaccgta aaaaggccgc gttgctggcg ttttttccata ggctccgccc    5100 ccctgacgag catcacaaaa atcgacgctc aagtcagagg tggcgaaacc cgacaggact    5160
ataaagatac caggcgtttc ccctggaag ctccctcgtg cgctctcctg ttccgaccct    5220
gccgcttacc ggatacctgt ccgcctttct cccttcggga agcgtggcgc tttctcatag    5280
ctcacgctgt aggtatctca gttcggtgta ggtcgttcgc tccaagctgg gctgtgtgca    5340 cgaaccccc gttcagcccg accgctgcgc cttatccggt aactatcgtc ttgagtccaa    5400
cccggtaaga cacgacttat cgccactggc agcagccact ggtaacagga ttagcagagc    5460
gaggtatgta ggcggtgcta cagagttctt gaagtggtgg cctaactacg gctacactag    5520
aagaacagta tttggtatct gcgctctgct gaagccagtt accttcggaa aaagagttgg    5580
tagctcttga tccggcaaac aaaccaccgc tggtagcggt ggtttttttg tttgcaagca    5640
gcagattacg cgcagaaaaa aaggatctca agaagatcct ttgatctttt ctacggggtc    5700
tgacgctcag tggaacgaaa actcacgtta agggattttg gtcatgagat tatcaaaaag    5760
gatcttcacc tagatccttt taaattaaaa atgaagtttt aaatcaatct aaagtatata    5820
tgagtaaact tggtctgaca gttaccaatg cttaatcagt gaggcaccta tctcagcgat    5880
ctgtctattt cgttcatcca tagttgcctg actccccgtc gtgtagataa ctacgatacg    5940
ggagggctta ccatctggcc ccagtgctgc aatgataccg cgagaaccac gctcaccggc    6000
tccagattta tcagcaataa accagccagc cggaagggcc gagcgcagaa gtggtcctgc    6060
aactttatcc gcctccatcc agtctattaa ttgttgccgg gaagctagag taagtagttc    6120
gccagttaat agtttgcgca acgttgttgc cattgctaca ggcatcgtgg tgtcacgctc    6180
gtcgtttggt atggcttcat tcagctccgg ttcccaacga tcaaggcgag ttacatgatc    6240
ccccatgttg tgcaaaaaag cggttagctc cttcggtcct ccgatcgttg tcagaagtaa    6300
gttggccgca gtgttatcac tcatggttat ggcagcactg cataattctc ttactgtcat    6360
```

-continued

```
gccatccgta agatgctttt ctgtgactgg tgagtactca accaagtcat tctgagaata    6420
gtgtatgcgg cgaccgagtt gctcttgccc ggcgtcaata cgggataata ccgcgccaca    6480
tagcagaact ttaaaagtgc tcatcattgg aaaacgttct tcggggcgaa aactctcaag    6540
gatcttaccg ctgttgagat ccagttcgat gtaaccccact cgtgcaccca actgatcttc    6600
agcatctttt actttcacca gcgtttctgg gtgagcaaaa acaggaaggc aaaatgccgc    6660
aaaaaaggga taagggcga cacggaaatg ttgaatactc atactcttcc ttttcaata    6720 ttattgaagc atttatcagg gttattgtct catgagcgga tacatatttg aa           6772
```

<210> SEQ ID NO 12
<211> LENGTH: 681
<212> TYPE: PRT
<213> ORGANISM: Artificial Sequence
<220> FEATURE:
<223> OTHER INFORMATION: Artificial sequence for PD-L1 CAR and CD16 fusion protein
<220> FEATURE:
<221> NAME/KEY: CD8 hinge
<222> LOCATION: (273)..(336)
<220> FEATURE:
<221> NAME/KEY: CD28 transmembrane
<222> LOCATION: (337)..(364)
<220> FEATURE:
<221> NAME/KEY: FceRIg signaling domain
<222> LOCATION: (365)..(405)
<220> FEATURE:
<221> NAME/KEY: P2A sequence
<222> LOCATION: (406)..(427)
<220> FEATURE:
<221> NAME/KEY: CD16 sequence
<222> LOCATION: (428)..(681)

<400> SEQUENCE: 12

Met Asp Trp Ile Trp Arg Ile Leu Phe Leu Val Gly Ala Ala Thr Gly
1               5                   10                  15

Ala His Ser Ala Gln Pro Ala Asn Ile Gln Met Thr Gln Ser Pro Ser
            20                  25                  30

Ser Val Ser Ala Ser Val Gly Asp Arg Val Thr Ile Thr Cys Arg Ala
        35                  40                  45

Ser Gln Asp Ile Ser Arg Trp Leu Ala Trp Tyr Gln Gln Lys Pro Gly
    50                  55                  60

Lys Ala Pro Lys Leu Leu Ile Tyr Ala Ala Ser Ser Leu Gln Ser Gly
65                  70                  75                  80

Val Pro Ser Arg Phe Ser Gly Ser Gly Ser Gly Thr Asp Phe Ala Leu
                85                  90                  95

Thr Ile Ser Ser Leu Gln Pro Glu Asp Phe Ala Thr Tyr Tyr Cys Gln
            100                 105                 110

Gln Ala Asp Ser Arg Phe Ser Ile Thr Phe Gly Gln Gly Thr Arg Leu
        115                 120                 125

Glu Ile Lys Gly Gly Gly Gly Ser Gly Gly Gly Gly Ser Gly Gly Gly
    130                 135                 140

Gly Ser Gly Gly Gly Gly Ser Glu Val Gln Leu Val Gln Ser Gly Gly
145                 150                 155                 160

Gly Leu Val Gln Pro Gly Gly Ser Leu Arg Leu Ser Cys Ala Ala Ser
                165                 170                 175

Gly Phe Thr Phe Ser Ser Tyr Ser Met Asn Trp Val Arg Gln Ala Pro
            180                 185                 190

Gly Lys Gly Leu Glu Trp Val Ser Tyr Ile Ser Ser Ser Ser Ser Thr
        195                 200                 205

```
Ile Gln Tyr Ala Asp Ser Val Lys Gly Arg Phe Thr Ile Ser Arg Asp
210                 215                 220

Asn Ala Lys Asn Ser Leu Tyr Leu Gln Met Asn Ser Leu Arg Asp Glu
225                 230                 235                 240

Asp Thr Ala Val Tyr Tyr Cys Ala Arg Gly Asp Tyr Tyr Gly Met
                245                 250                 255

Asp Val Trp Gly Gln Gly Thr Thr Val Thr Val Ser Ser Ala Ala Ala
            260                 265                 270

Leu Ser Asn Ser Ile Met Tyr Phe Ser His Phe Val Pro Val Phe Leu
            275                 280                 285

Pro Ala Lys Pro Thr Thr Thr Pro Ala Pro Arg Pro Pro Thr Pro Ala
290                 295                 300

Pro Thr Ile Ala Ser Gln Pro Leu Ser Leu Arg Pro Glu Ala Cys Arg
305                 310                 315                 320

Pro Ala Ala Gly Gly Ala Val His Thr Arg Gly Leu Asp Phe Ala Cys
                325                 330                 335

Phe Trp Val Leu Val Val Val Gly Gly Val Leu Ala Cys Tyr Ser Leu
                340                 345                 350

Leu Val Thr Val Ala Phe Ile Ile Phe Trp Val Arg Leu Lys Ile Gln
            355                 360                 365

Val Arg Lys Ala Ala Ile Thr Ser Tyr Glu Lys Ser Asp Gly Val Tyr
370                 375                 380

Thr Gly Leu Ser Thr Arg Asn Gln Glu Thr Tyr Glu Thr Leu Lys His
385                 390                 395                 400

Glu Lys Pro Pro Gln Gly Ser Gly Ala Thr Asn Phe Ser Leu Leu Lys
                405                 410                 415

Gln Ala Gly Asp Val Glu Glu Asn Pro Gly Pro Met Trp Gln Leu Leu
            420                 425                 430

Leu Pro Thr Ala Leu Leu Leu Leu Val Ser Ala Gly Met Arg Thr Glu
            435                 440                 445

Asp Leu Pro Lys Ala Val Val Phe Leu Glu Pro Gln Trp Tyr Arg Val
450                 455                 460

Leu Glu Lys Asp Ser Val Thr Leu Lys Cys Gln Gly Ala Tyr Ser Pro
465                 470                 475                 480

Glu Asp Asn Ser Thr Gln Trp Phe His Asn Glu Ser Leu Ile Ser Ser
                485                 490                 495

Gln Ala Ser Ser Tyr Phe Ile Asp Ala Ala Thr Val Asp Asp Ser Gly
            500                 505                 510

Glu Tyr Arg Cys Gln Thr Asn Leu Ser Thr Leu Ser Asp Pro Val Gln
            515                 520                 525

Leu Glu Val His Ile Gly Trp Leu Leu Leu Gln Ala Pro Arg Trp Val
530                 535                 540

Phe Lys Glu Glu Asp Pro Ile His Leu Arg Cys His Ser Trp Lys Asn
545                 550                 555                 560

Thr Ala Leu His Lys Val Thr Tyr Leu Gln Asn Gly Lys Gly Arg Lys
                565                 570                 575

Tyr Phe His His Asn Ser Asp Phe Tyr Ile Pro Lys Ala Thr Leu Lys
            580                 585                 590

Asp Ser Gly Ser Tyr Phe Cys Arg Gly Leu Val Gly Ser Lys Asn Val
            595                 600                 605

Ser Ser Glu Thr Val Asn Ile Thr Ile Thr Gln Gly Leu Ala Val Ser
610                 615                 620
```

```
Thr Ile Ser Ser Phe Phe Pro Pro Gly Tyr Gln Val Ser Phe Cys Leu
625                 630                 635                 640

Val Met Val Leu Leu Phe Ala Val Asp Thr Gly Leu Tyr Phe Ser Val
                645                 650                 655

Lys Thr Asn Ile Arg Ser Ser Thr Arg Asp Trp Lys Asp His Lys Phe
            660                 665                 670

Lys Trp Arg Lys Asp Pro Gln Asp Lys
675                 680
```

<210> SEQ ID NO 13
<211> LENGTH: 160
<212> TYPE: PRT
<213> ORGANISM: Artificial Sequence
<220> FEATURE:
<223> OTHER INFORMATION: Artificial sequence of erIL2

<400> SEQUENCE: 13

```
Met Tyr Arg Met Gln Leu Leu Ser Cys Ile Ala Leu Ser Leu Ala Leu
1               5                   10                  15

Val Thr Asn Ser Ala Pro Thr Ser Ser Ser Thr Lys Lys Thr Gln Leu
                20                  25                  30

Gln Leu Glu His Leu Leu Leu Asp Leu Gln Met Ile Leu Asn Gly Ile
            35                  40                  45

Asn Asn Tyr Lys Asn Pro Lys Leu Thr Arg Met Leu Thr Phe Lys Phe
50                  55                  60

Tyr Met Pro Lys Lys Ala Thr Glu Leu Lys His Leu Gln Cys Leu Glu
65                  70                  75                  80

Glu Glu Leu Lys Pro Leu Glu Glu Val Leu Asn Leu Ala Gln Ser Lys
                85                  90                  95

Asn Phe His Leu Arg Pro Arg Asp Leu Ile Ser Asn Ile Asn Val Ile
            100                 105                 110

Val Leu Glu Leu Lys Gly Ser Glu Thr Thr Phe Met Cys Glu Tyr Ala
        115                 120                 125

Asp Glu Thr Ala Thr Ile Val Glu Phe Leu Asn Arg Trp Ile Thr Phe
    130                 135                 140

Cys Gln Ser Ile Ile Ser Thr Leu Thr Gly Ser Glu Lys Asp Glu Leu
145                 150                 155                 160
```

<210> SEQ ID NO 14
<211> LENGTH: 1215
<212> TYPE: DNA
<213> ORGANISM: Artificial Sequence
<220> FEATURE:
<223> OTHER INFORMATION: Artificial sequence encoding PD-L1 CAR

<400> SEQUENCE: 14

```
atggactgga tctggcggat tctgtttctc gtgggagctg ccacaggcgc tcattctgct      60
cagcctgcca acatccagat gacccagtct ccatcttctg tgtctgcatc tgtaggagac     120
agagtcacca tcacttgtcg ggcgagtcag gatattagcc gctggttagc ctggtatcag     180
cagaaaccag ggaaagcccc taaactcctg atctatgctg catccagttt gcaaagtggg     240
gtcccatcga ggttcagcgg cagtggatct gggacagatt tcgctctcac tatcagcagc     300
ctgcagcctg aagattttgc aacttactat tgtcaacagg ctgacagtcg tttctcgatc     360
accttcggcc aagggacacg actggagatt aaaggcggcg gaggaagcgg aggcggagga     420
tctggggccg gaggctctgg cggaggggga tctgaggtgc agctggtgca gtctggggga     480
ggcttggtac agcctggggg gtccctgaga ctctcctgtg cagcctctgg attcaccttc     540
```

```
agtagctata gcatgaactg ggtccgccag gctccaggga aggggctgga gtgggtttca    600
tacattagta gtagtagtag taccatacag tacgcagact ctgtgaaggg ccgattcacc    660
atctccagag acaatgccaa gaactcactg tatctgcaaa tgaacagcct gagagacgag    720
gacacggctg tgtattactg tgcgagaggg gactactact acggtatgga cgtctggggc    780
caagggacca cggtcaccgt gagctcagcg gccgcgctga gcaacagcat catgtacttc    840
agccacttcg tgcctgtgtt cctgcctgcc aagcctacaa caacaccagc cctagacct     900 ccaacccctg cccctacaat gcctctcag cctctgtctc tgaggcccga agcttgtaga    960
cctgctgctg gcggagctgt gcacaccaga ggactggatt tcgcctgctt ttgggtgctg   1020
gtggtcgtgg gcggagtgct ggcttgttat tctctgctgg tcaccgtggc cttcatcatc   1080
ttttgggtcc gactgaagat ccaggtccga aaggccgcca tcaccagcta cgagaagtct   1140
gatggcgtgt acaccggcct gagcaccaga accaggaaa cctacgagac actgaagcac    1200
gagaagcccc cccag                                                    1215
```

<210> SEQ ID NO 15
<211> LENGTH: 405
<212> TYPE: PRT
<213> ORGANISM: Artificial Sequence
<220> FEATURE:
<223> OTHER INFORMATION: Artificial sequenc for PD-L1 CAR

<400> SEQUENCE: 15

```
Met Asp Trp Ile Trp Arg Ile Leu Phe Leu Val Gly Ala Ala Thr Gly
1               5                   10                  15

Ala His Ser Ala Gln Pro Ala Asn Ile Gln Met Thr Gln Ser Pro Ser
            20                  25                  30

Ser Val Ser Ala Ser Val Gly Asp Arg Val Thr Ile Thr Cys Arg Ala
        35                  40                  45

Ser Gln Asp Ile Ser Arg Trp Leu Ala Trp Tyr Gln Gln Lys Pro Gly
    50                  55                  60

Lys Ala Pro Lys Leu Leu Ile Tyr Ala Ala Ser Ser Leu Gln Ser Gly
65                  70                  75                  80

Val Pro Ser Arg Phe Ser Gly Ser Gly Ser Gly Thr Asp Phe Ala Leu
                85                  90                  95

Thr Ile Ser Ser Leu Gln Pro Glu Asp Phe Ala Thr Tyr Tyr Cys Gln
            100                 105                 110

Gln Ala Asp Ser Arg Phe Ser Ile Thr Phe Gly Gln Gly Thr Arg Leu
        115                 120                 125

Glu Ile Lys Gly Gly Gly Gly Ser Gly Gly Gly Gly Ser Gly Gly Gly
    130                 135                 140

Gly Ser Gly Gly Gly Gly Ser Glu Val Gln Leu Val Gln Ser Gly Gly
145                 150                 155                 160

Gly Leu Val Gln Pro Gly Gly Ser Leu Arg Leu Ser Cys Ala Ala Ser
                165                 170                 175

Gly Phe Thr Phe Ser Ser Tyr Ser Met Asn Trp Val Arg Gln Ala Pro
            180                 185                 190

Gly Lys Gly Leu Glu Trp Val Ser Tyr Ile Ser Ser Ser Ser Ser Thr
        195                 200                 205

Ile Gln Tyr Ala Asp Ser Val Lys Gly Arg Phe Thr Ile Ser Arg Asp
    210                 215                 220

Asn Ala Lys Asn Ser Leu Tyr Leu Gln Met Asn Ser Leu Arg Asp Glu
225                 230                 235                 240
```

-continued

```
Asp Thr Ala Val Tyr Tyr Cys Ala Arg Gly Asp Tyr Tyr Tyr Gly Met
            245                 250                 255

Asp Val Trp Gly Gln Gly Thr Thr Val Thr Val Ser Ser Ala Ala Ala
        260                 265                 270

Leu Ser Asn Ser Ile Met Tyr Phe Ser His Phe Val Pro Val Phe Leu
        275                 280                 285

Pro Ala Lys Pro Thr Thr Thr Pro Ala Pro Arg Pro Pro Thr Pro Ala
    290                 295                 300

Pro Thr Ile Ala Ser Gln Pro Leu Ser Leu Arg Pro Glu Ala Cys Arg
305                 310                 315                 320

Pro Ala Ala Gly Gly Ala Val His Thr Arg Gly Leu Asp Phe Ala Cys
                325                 330                 335

Phe Trp Val Leu Val Val Val Gly Gly Val Leu Ala Cys Tyr Ser Leu
                340                 345                 350

Leu Val Thr Val Ala Phe Ile Ile Phe Trp Val Arg Leu Lys Ile Gln
        355                 360                 365

Val Arg Lys Ala Ala Ile Thr Ser Tyr Glu Lys Ser Asp Gly Val Tyr
    370                 375                 380

Thr Gly Leu Ser Thr Arg Asn Gln Glu Thr Tyr Glu Thr Leu Lys His
385                 390                 395                 400

Glu Lys Pro Pro Gln
                405
```

ELIMINATION OF PD-L1-POSITIVE MALIGNANCIES BY PD-L1 CHIMERIC ANTIGEN RECEPTOR-EXPRESSING NK CELLS

This application claims priority to our US Provisional patent application with the Ser. No. 62/753,740, which was filed Oct. 31, 2018, and which is incorporated by reference herein.

SEQUENCE LISTING

The content of the ASCII text file of the sequence listing named 104077_0006 PCT_ST25_REV006, which is 40 kb in size was created on Jul. 26, 2019 and electronically submitted via EFS-Web along with the present application is incorporated by reference in its entirety.

BACKGROUND

Cancer cells in a solid tumor are able to form a tumor microenvironment in their surroundings to support the growth and metastasis of the cancer cells. A tumor microenvironment is the cellular environment in which the tumor exists, including surrounding blood vessels, immune cells, fibroblasts, other cells, soluble factors, signaling molecules, an extracellular matrix, and mechanical cues that can promote neoplastic transformation, support tumor growth and invasion, protect the tumor from host immunity, foster therapeutic resistance, and provide niches for dormant metastases to thrive. The tumor and its surrounding microenvironment are closely related and interact constantly. Tumors can influence their microenvironment by releasing extracellular signals, promoting tumor angiogenesis and inducing peripheral immune tolerance, while the immune cells in the microenvironment can affect the growth and evolution of cancerous cells. See Swarts et al. "Tumor Microenvironment Complexity: Emerging Roles in Cancer Therapy," Cancer Res, vol., 72, pages 2473-2480, 2012.

Natural killer (NK) cells are cytotoxic lymphocytes that constitute a major component of the innate immune system. Natural killer (NK) cells, generally representing about 10-15% of circulating lymphocytes, bind and kill targeted cells, including virus-infected cells and many malignant cells, non-specifically with regard to antigen and without prior immune sensitization. Herberman et al., Science 214: 24 (1981) Killing of targeted cells occurs by inducing cell lysis. NK cells used for this purpose are isolated from the peripheral blood lymphocyte ("PBL") fraction of blood from the subject, expanded in cell culture in order to obtain sufficient numbers of cells, and then re-infused into the subject. Such autologous NK cells have shown some effectiveness in both ex vivo therapy and in vivo treatment. However, such therapy is limited to autologous contexts, and further complicated by the fact that not all NK cells are cytolytic.

Currently, CAR-T therapy has become the common therapy for targeting immune cells in the tumor microenvironment. However, because many of the target antigens are also expressed on normal precursor cells, these CAR-T therapies often cause cytopenias and reduction of myeloid progenitors in in vivo models, suggesting that permanently expressed tumor antigen-specific CAR-T cells would have unacceptable toxicity for the patients. In addition, CAR-T technology relies on engineering autologous T-cells, which results in significant patient-to-patient variability, as well as exclusion of a number of patients whose T-cells cannot be expanded. Thus, a need remains for an effective cancer therapy that target both the tumor cells and the cells in the tumor microenvironment.

BRIEF SUMMARY

In some embodiments, this disclosure provides a modified NK-92® cell expressing a PD-L1 CAR and a Fc receptor. In some embodiments, the modified NK-92® cell comprises a multi-cistronic construct and wherein the multi-cistronic construct encodes the PD-L1 CAR and the Fc receptor. In some embodiments, the Fc receptor is a CD16. In some embodiments, the Fc receptor comprises SEQ ID NO: 2. In some embodiments, the multi-cistronic transgene further comprises a sequence that encodes an IL-2 or a variant thereof. In some embodiments, the PD-L1 CAR, the Fc receptor, and/or the IL2 are encoded by codon-optimized nucleic acid sequence. In some embodiments, the IL-2 variant is erIL-2.

In some embodiments, the coding sequences for one or more of the PD-L1 CAR, the Fc receptor, or erIL-2 are codon-optimized for expression in a human system. In some embodiments, the modified NK-92® cell is capable of killing a PD-L1-expressing cell. In some embodiments, the PD-L1-expressing cell is a myeloid-derived suppressor cell (MDSC), or a tumor cell. In some embodiments, the PD-L1 CAR comprises a scFv antibody fragment. In some embodiments, the modified NK-92® cell comprises a sequence encoding a self-cleaving peptide, wherein the sequence is located between the PD-L1 CAR and CD16, and wherein the sequence allows equimolar expression of the PD-L1 CAR and the FcR. In some embodiments, the modified NK-92® cell comprises an internal ribosomal entry sequence (IRES) between the sequence encoding CD16 and the sequence encoding IL-2 or a variant thereof.

In some embodiments, the direct cytotoxicity of the modified NK-92 cell on PD-L1-expressing cells is 40-100% when the effector to target ratio is 10. In some embodiments, the direct cytotoxicity of the modified NK-92® cell on PD-L1 expressing cells is higher than of the aNK® cell. In some embodiments, the ADCC activity of the modified NK-92® cell is at 20%-60% when the effector to target ratio is 10. In some embodiments, the PD-L1 CAR comprises a sequence that shares at least 90% identity to SEQ ID NO: 10 (and particularly to the CDR sequences within SEQ ID NO:10). In some embodiments, this disclosure provides a kit comprising a pharmaceutical composition comprising the modified NK-92® cell disclosed above. In some embodiments, this disclosure provides a method for generating a modified NK92® cell comprising providing a vector, wherein the vector encodes a PD-L1 CAR and a CD16, and introducing the vector into the NK-92® cells to generate the modified NK-92® cell.

In some embodiments, the vector further comprises a sequence that encodes an IL-2. In some embodiments, the vector comprises a sequence encoding a self-cleaving peptide, wherein the sequence is located between CAR and CD16, and wherein the sequence allows equimolar expression of CAR and CD16. In some embodiments, the vector comprises an internal ribosomal entry sequence (IRES) between the CD16 coding sequence and the IL-2 coding sequence. In some embodiments, this disclosure provides a method for killing a PD-L1 expressing cell, comprising incubating the myeloid-derived suppressor cells (MDSC), tumor associated macrophages (TAM), or tumor cells with a plurality of modified NK-92® cells of any of claims 1-17, whereby killing the MDSC, the TAM, or the tumor cell.

In some embodiments, the PD-L1 expressing cell is a tumor cell or a cell in a tumor microenvironment. In some embodiments, the cell in the microenvironment is a myeloid-derived suppressor cell (MDSC) or a tumor associated macrophage (TAM). In some embodiments, the MDSC cell express CD14 or CD15. In some embodiments, the TAM express CD68 and one or more of the CD206, CD204, or CD163. In some embodiments, this disclosure provides a method for killing myeloid-derived suppressor cells (MDSC), tumor associated macrophages, or tumor cells in a subject, comprising administering a therapeutically effective amount of a composition to the subject, the composition comprising a plurality of the modified NK-92® cells described above.

In some embodiments, about $1\times10^8$ to about $1\times10^{11}$ modified cells per m² of body surface area of the subject are administered to the subject. In some embodiments, this disclosure provides a method of treating a cancer in a subject, comprising administering to the subject a therapeutically effective amount of a composition to the subject, the composition comprising a plurality of any of the modified NK-92® cells described above. In some embodiments, the cancer is selected from the group consisting of melanoma, breast cancer, ovarian cancer, gastric cancer, prostate cancer, squamous cell carcinoma, head and neck cancer, colon cancer, pancreatic cancer, uterine cancer, renal cell cancer, glioblastoma, medulloblastoma, sarcoma, and lung cancer. In some embodiments, the cells are administered intravenously. In some embodiments, the cells are administered intratumorally.

In some embodiments, this disclosure provides a method for killing myeloid-derived suppressor cells (MDSC) or tumor cells in a subject, comprising administering a therapeutically effective amount of a first composition and a second composition to the subject, wherein the first composition comprises a plurality of NK-92® cells, wherein the second composition comprises an anti-PD-L1 antibody.

In some embodiments, the NK-92® cells express a Fc receptor. In some embodiments, the NK-92® cells are haNK® cells. In some embodiments, the second composition is Avelumab.

The foregoing general description and the following detailed description are exemplary and explanatory and are intended to provide further explanation of the disclosure. Other objects, advantages and novel features will be readily apparent to those skilled in the art.

BRIEF DESCRIPTION OF THE DRAWINGS

The objects, features and advantages will be more readily appreciated upon reference to the following disclosure when considered in conjunction with the accompanying drawings.

DETAILED DESCRIPTION

Overview

Figure 1:
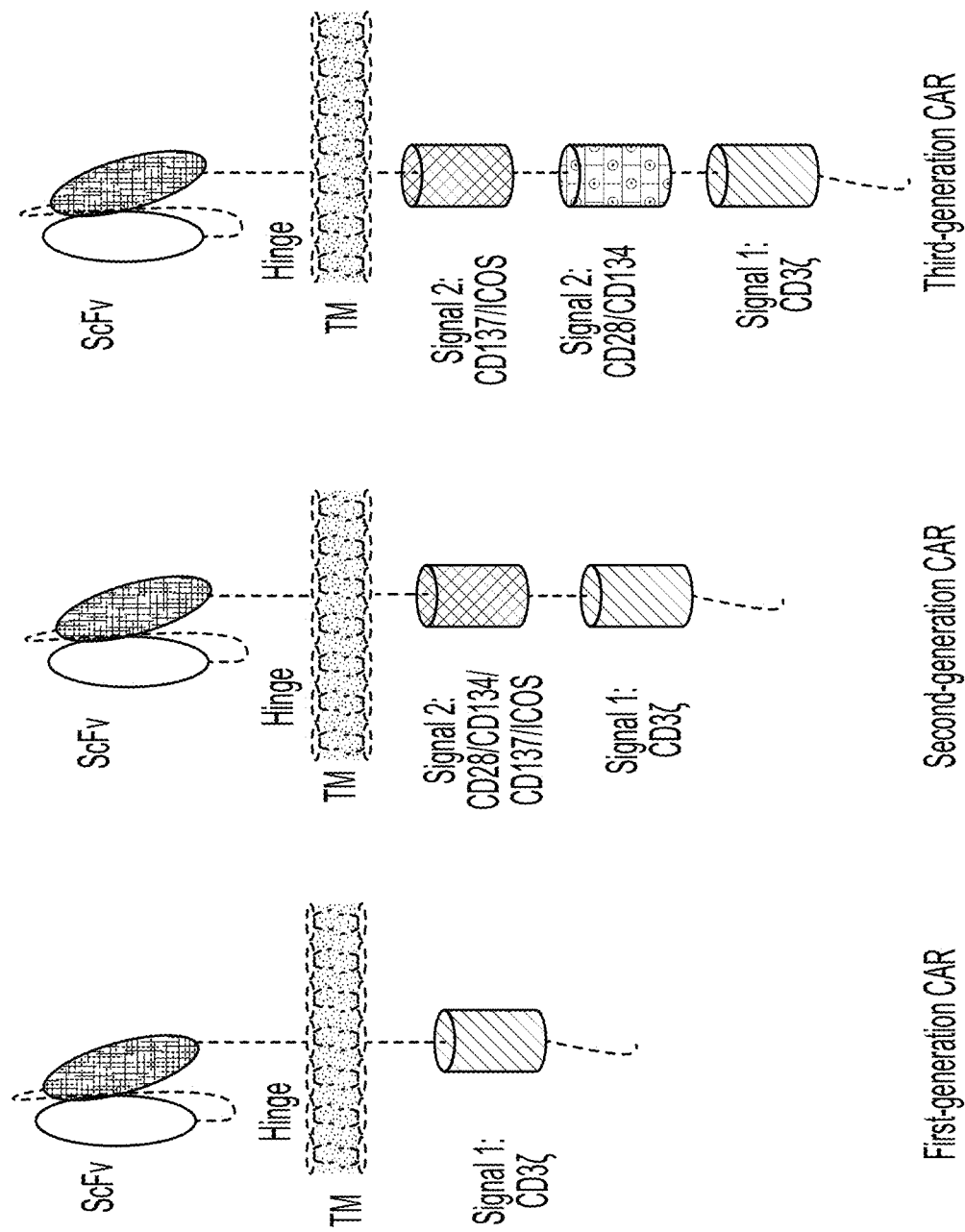
FIG. 1 is a schematic representation of the structure domains of first, second, and third-generation of CARs.

This disclosure provides NK-92™ cells that express a combination of a PD-L1 CAR, a Fc receptor, and an IL2. These cells can target both tumor cells and cells in the tumor microenvironment, effectively treating cancer.

Terminology

Unless defined otherwise, all technical and scientific terms used herein have the same meaning as commonly understood by one of ordinary skill in the art.

In this specification and in the claims that follow, reference will be made to a number of terms that shall be defined to have the following meanings:

The terminology used herein is for the purpose of describing particular embodiments only and is not intended to be limiting. As used herein, the singular forms "a," "an" and "the" are intended to include the plural forms as well, unless the context clearly indicates otherwise. Thus, for example, reference to "a natural killer cell" includes a plurality of natural killer cells.

All numerical designations, e.g., pH, temperature, time, concentration, amounts, and molecular weight, including ranges, are approximations which are varied (+) or (−) by increments of 0.1 or 1.0, where appropriate. It is to be understood, although not always explicitly stated, that all numerical designations may be preceded by the term "about."

As used herein, "+", when used to indicate the presence of a particular cellular marker, means that the cellular marker is detectably present in fluorescence activated cell sorting over an isotype control; or is detectable above background in quantitative or semi-quantitative RT-PCR.

As used herein, "−", when used to indicate the presence of a particular cellular marker, means that the cellular marker is not detectably present in fluorescence activated cell sorting over an isotype control; or is not detectable above background in quantitative or semi-quantitative RT-PCR.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like, include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

As used herein, the term "substantially the same", used interchangeably with the term "comparable", or "substantially similar", when referring to certain quantifiable properties of the NK-92™ cells, such as cytotoxicity, viability or cell doubling time, etc., refers to the that the two measurements of these properties are no more than 15% different, no more than 10%, no more than 8%, or no more than 5% different from each other.

It is also to be understood, although not always explicitly stated, that the reagents described herein are merely exemplary and that equivalents of such are known in the art.

For purposes of this invention and unless indicated otherwise, the term "NK-92™" is intended to refer to the original NK-92™ cell lines as well as NK-92™ cell lines, clones of NK-92™ cells, and NK-92™ cells that have been modified (e.g., by introduction of exogenous genes). NK-92™ cells and exemplary and non-limiting modifications thereof are described in U.S. Pat. Nos. 7,618,817; 8,034,332; 8,313,943; 9,181,322; 9,150,636; and published U.S. application Ser. No. 10/008,955, all of which are incorporated herein by reference in their entireties, and include wild type NK-92™, NK-92™-CD16, NK-92™-CD16-γ, NK-92™-CD16-ζ, NK-92™-CD16(F176V), NK-92™ MI, and NK-92™ CI. NK-92™ cells are known to persons of ordinary skill in the art, to whom such cells are readily available from NantKwest, Inc.

As used herein, the term "NK-92™ cells" refers to natural killer cells derived from the highly potent unique cell line described in Gong et al. (Leukemia, April; 8(4): 652-8 (1994)), rights to which are owned by NantKwest (hereafter, "NK-92™ cells")

As used herein, the term "aNK™ cells" refers to unmodified natural killer cells derived from the highly potent unique cell line described in Gong et al. (Leukemia, April; 8(4): 652-8 (1994)), rights to which are owned by NantKwest (hereafter, "aNK™ cells")

As used herein, the term "haNK® cells" refers to natural killer cells derived from the highly potent unique cell line described in Gong et al. (Leukemia, April; 8(4): 652-8 (1994)), rights to which are owned by NantKwest, modified to express CD16 on the cell surface (hereafter, "CD16+NK-92™ cells" or "haNK® cells")

As used herein, the term "taNK® cells" refers to natural killer cells derived from the highly potent unique cell line described in Gong et al. (Leukemia, April; 8(4): 652-8 (1994)), rights to which are owned by NantKwest, modified to express a chimeric antigen receptor (hereafter, "CAR-modified NK-92™ cells" or "taNK® cells")

As used herein, the term "t-haNK™" cells refers to natural killer cells derived from the highly potent unique cell line described in Gong et al. (Leukemia, April; 8(4): 652-8 (1994)), which are owned by NantkWest, modified to express CD16 on the cell surface and to express a chimeric antigen receptor (hereafter, "CAR-modified CD16+NK-92™ cells" or "t-haNK cells"). In some embodiments, the tumor specific antigen is PD-L1, and these NK-92™ cells are referred to as PD-L1 t-haNK cells.

As used herein, the term "multi-cistronic construct," refers to a recombinant DNA construct that is to be transcribed into a single mRNA molecule and the single mRNA molecule encodes two or more transgenes. The multi-cistronic construct is referred to as bicistronic construct if it encodes two transgenes, and tricistronic construct if it encodes three genes, and quadrocistronic construct if it encodes four genes, and so on.

The term "chimeric antigen receptor" (CAR), as used herein, refers to an extracellular antigen-binding domain that is fused to an intracellular signaling domain. CARs can be expressed in T cells or NK cells to increase cytotoxicity. In general, the extracellular antigen-binding domain is a scFv that is specific for an antigen found on a cell of interest. A CAR-expressing NK-92™ cell is targeted to cells expressing certain antigens on the cell surface, based on the specificity of the scFv domain. The scFv domain can be engineered to recognize any antigen, including tumor-specific antigens and virus-specific antigens. For example, PD-L1 CAR recognizes PD-L1, a cell surface marker expressed by some cancers.

The term "tumor-specific antigen" as used herein refers to antigens that are present on a cancer or neoplastic cell but not detectable on a normal cell derived from the same tissue or lineage as the cancer cell. Tumor-specific antigens, as used herein, also refers to tumor-associated antigens, that is, antigens that are expressed at a higher level on a cancer cell as compared to a normal cell derived from the same tissue or lineage as the cancer cell.

As used herein, the term "target," when referring to targeting of a tumor, refers to the ability of NK-92™ cells to recognize and kill a tumor cell (i.e., target cell). The term "targeted" in this context refers, for example, to the ability of a CAR expressed by the NK-92™ cell to recognize and bind to a cell surface antigen expressed by the tumor.

The term "antibody" refers to an intact immunoglobulin of any isotype, or a fragment thereof that can compete with the intact antibody for specific binding to the target antigen, and includes chimeric, humanized, fully human, and bispecific antibodies. An intact antibody generally comprises at least two full-length heavy chains and two full-length light chains, but in some instances can include fewer chains such as antibodies naturally occurring in camelids which can comprise only heavy chains. Antibodies can be derived solely from a single source, or can be "chimeric," such that different portions of the antibody are derived from two different antibodies. The antigen binding proteins, antibodies, or binding fragments can be produced in hybridomas, by recombinant DNA techniques, or by enzymatic or chemical cleavage of intact antibodies. Unless otherwise indicated, the term "antibody" includes, in addition to antibodies comprising two full-length heavy chains and two full-length light chains, derivatives, variants, fragments, and muteins thereof. Furthermore, unless explicitly excluded, antibodies include monoclonal antibodies, bispecific antibodies, minibodies, domain antibodies, synthetic antibodies (sometimes referred to herein as "antibody mimetics"), chimeric antibodies, humanized antibodies, human antibodies, antibody fusions (sometimes referred to herein as "antibody conjugates"), and fragments thereof, respectively. In some embodiments, the term also includes peptibodies.

The term "subject' refers to a non-human animal, including mammals, such as cats, dogs, cows, horses, pigs, sheep, and goats, and humans. The term subject also refers to a patient in need of treatment for a disease described herein.

"Optional" or "optionally" means that the subsequently described event or circumstance can or cannot occur, and that the description includes instances where the event or circumstance occurs and instances where it does not.

The term "comprising" is intended to mean that the compositions and methods include the recited elements, but not excluding others. "Consisting essentially of," when used to define compositions and methods, shall mean excluding other elements of any essential significance to the combination. For example, a composition consisting essentially of the elements as defined herein would not exclude other elements that do not materially affect the basic and novel characteristic(s) of the claims. "Consisting of" means excluding more than trace amount of other ingredients and substantial method steps. Embodiments defined by each of these transition terms are within the scope of the disclosure.

As used herein, the terms "cytotoxic" and "cytolytic", when used to describe the activity of effector cells such as NK cells, are intended to be synonymous. In general, cytotoxic activity relates to killing of target cells by any of a variety of biological, biochemical, or biophysical mechanisms. Cytolysis refers more specifically to activity in which the effector lyses the plasma membrane of the target cell, thereby destroying its physical integrity. This results in the killing of the target cell. Without wishing to be bound by theory, it is believed that the cytotoxic effect of NK cells is due to cytolysis.

The term "kill" with respect to a cell/cell population is directed to include any type of manipulation that will lead to the death of that cell/cell population.

The term "cytokine" or "cytokines" refers to the general class of biological molecules which effect cells of the immune system. Exemplary cytokines include but are not limited to FLT3 ligand, interferons and interleukins (IL), in particular IL-2, IL-12, IL-15, IL-18 and IL-21.

The terms "patient," "subject," "individual," and the like are used interchangeably herein, and refer to any animal, or cells thereof whether in vitro or in situ, amenable to the methods described herein. In certain non-limiting embodiments, the patient, subject or individual is a human.

The term "treating" or "treatment" covers the treatment of a disease or disorder described herein, in a subject, such as a human, and includes: (i) inhibiting a disease or disorder, i.e., arresting its development; (ii) relieving a disease or disorder, i.e., causing regression of the disorder; (iii) slowing progression of the disorder; and/or (iv) inhibiting, relieving, or slowing progression of one or more symptoms of the disease or disorder. The term "administering" or "administration" of a monoclonal antibody or a natural killer cell to a subject includes any route of introducing or delivering the antibody or cells to perform the intended function. Administration can be carried out by any route suitable for the delivery of the cells or monoclonal antibody. Thus, delivery routes can include intravenous, intramuscular, intraperitoneal, or subcutaneous delivery. In some embodiments the modified NK-92™ cells are administered directly to the tumor, e.g., by injection into the tumor. In some embodiments the modified NK-92™ cells described herein are administered parenterally, e.g., by injection, infusion or implantation (subcutaneous, intravenous, intramuscular, intravesicularly, or intraperitoneal).

The term "expression" refers to the production of a gene product.

As used herein, the terms "cytotoxic" when used to describe the activity of effector cells such as NK cells, relates to killing of target cells by any of a variety of biological, biochemical, or biophysical mechanisms.

The terms "decrease," "reduced," "reduction," and "decrease" are all used herein to refer to a decrease by at least 10% as compared to a reference level, for example a decrease by at least about 20%, or at least about 30%, or at least about 40%, or at least about 50%, or at least about 60%, or at least about 70%, or at least about 80%, or at least about 90% or up to and including a 100% decrease (i.e. absent level as compared to a reference sample), or any decrease between 10-100% as compared to a reference level.

The term "cancer" refers to all types of cancer, neoplasm, or malignant tumors found in mammals, including leukemia, carcinomas and sarcomas. Exemplary cancers include cancer of the brain, breast, cervix, colon, head & neck, liver, kidney, lung, non-small cell lung, melanoma, mesothelioma, ovary, sarcoma, stomach, uterus and medulloblastoma. Additional examples include, Hodgkin's Disease, Non-Hodgkin's Lymphoma, multiple myeloma, neuroblastoma, ovarian cancer, rhabdomyosarcoma, primary thrombocytosis, primary macroglobulinemia, primary brain tumors, cancer, malignant pancreatic insulanoma, malignant carcinoid, urinary bladder cancer, premalignant skin lesions, testicular cancer, lymphomas, thyroid cancer, neuroblastoma, esophageal cancer, genitourinary tract cancer, malignant hypercalcemia, endometrial cancer, adrenal cortical cancer, neoplasms of the endocrine and exocrine pancreas, and prostate cancer.

The term "therapeutically effective amount" or "effective amount" refers to the amount required to ameliorate the symptoms of a disease relative to an untreated patient. The effective amount of active compound(s) used to practice the present disclosure for therapeutic treatment of a disease varies depending upon the manner of administration, the age, body weight, and general health of the subject. Ultimately, the attending physician or veterinarian will decide the appropriate amount and dosage regimen. Such amount is referred to as an "effective" amount.

The term "tumor microenvironment" refers to a cellular environment in which the tumor exists, including surrounding blood vessels, immune cells, fibroblasts, bone marrow-derived inflammatory cells, signaling molecules and the extracellular matrix. Exemplary types of cells in tumor microenvironment include, but are not limited to, myeloid derived suppressor cells (MDSC) and tumor associated macrophages (TAMs).

The term "immune cells" refers to cells of hematopoietic origin that are involved in the specific recognition of antigens Immune cells include antigen presenting cells (APCs), such as dendritic cells or macrophages, B cells, T cells, natural killer cells, myeloid derived suppressor cells (MDSC), myeloid cells, such as monocytes, macrophages, eosinophils, mast cells, basophils, and granulocytes.

Titles or subtitles may be used in the specification for the convenience of a reader, which are not intended to influence the scope of the present disclosure. Additionally, some terms used in this specification are more specifically defined below.

MDSCS

The myeloid derived suppressor cells (MDSC), are one of the main suppressor cells in the tumor microenvironment. The microenvironment of tumors prevents immune active cells such as NK cells to interact with tumor cells, attack and kill them. These negative paralyzing effects can be mediated by metabolites and secretory product of suppressor cells that are present in the tumor microenvironment.

MDSCs are regulators of immune responses in cancer and other pathological conditions, such as myelodysplastic syndrome (MDS) (See, e.g., Bronte et al., Nature Communications, 6 Jul. 2016, 7:12150, DOI: 10.1038/ncomms12150; Eksioglu et al., "Novel Therapeutic Approach to Improve Hematopoiesis in low risk MDS by Targeting myeloid-derived suppressor cells with The Fc-engineered CD33 Antibody BI 836858," Leukemia. 2017 October; 31(10): 2172-2180. doi:10.1038/leu.2017.21). Myeloid-derived suppressor cells are a heterogenous group of immune cells from the myeloid lineage, such as early myeloid progenitors, immature granulocytes, macrophages and dendritic cells at different stages of differentiation. Myeloid-derived suppressor cells strongly expand in pathological situations such as chronic infections and cancer, as a result of an altered haematopoiesis (see, e.g., Eksioglu et al., "Novel Therapeutic Approach to Improve Hematopoiesis in low risk MDS by Targeting myeloid-derived suppressor cells with The Fc-engineered CD33 Antibody BI 836858," *Leukemia.* 2017 October; 31(10): 2172-2180. doi:10.1038/leu.2017.21).

Myeloid-derived suppressor cells are discriminated from other myeloid cell types in which they possess strong immunosuppressive activities rather than immunostimulatory properties. Similar to other myeloid cells, myeloid-derived suppressor cells interact with other immune cell types including T cells, dendritic cells, macrophages and natural killer cells to regulate their functions. Myeloid-derived suppressor cells can suppress both the cytotoxic activities of natural killer (NK) cells and NKT cells, and the adaptive immune response mediated by CD4+ and CD8+ T cells. Although their mechanisms of action are not well understood, clinical and experimental evidence has shown that cancer tissues with high infiltration of myeloid-derived suppressor cells are associated with poor patient prognosis and resistance to therapies.

Accumulation of MDSC in the peripheral circulation has been related to extent of disease, and correlates with stage. MDSC have primarily been implicated in promoting tumor growth by suppressing antitumor immunity. There is also compelling evidence MDSC are also involved in angiogenesis and metastatic spread.

Two main subsets of MDSC have been identified in cancer patients: a monocytic subset, characterized by expression of CD14, and a granulocytic subset characterized by expression of CD15. Both subsets of MDSC actively suppress host immunity through a variety of mechanisms including production of reactive oxygen species and arginase. Just as in humans, accumulation of monocytic and granulocytic MDSC has been noted in the bone marrow, spleen, peripheral circulation, and tumors of tumor bearing mice. Successful targeting of MDSC in mice is associated with improved immune responses, delayed tumor growth, improved survival, and increased efficacy of vaccine therapy. In the tumor monocytic derived MDSC rapidly differentiate to tumor associated macrophages (TAM).

Tumor Associated Macrophages

Tumors are often associated with an immune infiltrate as part of the reactive stroma that is enriched for macrophages. Typically macrophages are categorized into M1 and M2 macrophages, which have opposing effects on tumor growth: M1 macrophages inhibit tumor cell growth while M2 macrophages promote tumor development. Tumor cells coax macrophages to M2-like phenotype via chemokine and polarizing cytokines, aiding their escape from destruction, promoting their development. These M2 macrophages are commonly referred to as tumor-associated macrophages (TAMs). The TAMs reside in the tumor microenvironment and play an important role in facilitating tumor growth by promoting neovascularization and matrix degradation. Consequently, many tumors with a high number of TAMs have an increased tumor growth rate, local proliferation and distant metastasis.

TAMs express CD68 as well as other markers, for example, some TAMs express one or more of the following markers CD206, CD204, or CD163.

NK-92™ Cells

NK-92™ is a cytolytic cancer cell line which was discovered in the blood of a subject suffering from a non-Hodgkins lymphoma and then immortalized in vitro. NK-92™ cells are derived from NK cells, but lack the major inhibitory receptors that are displayed by normal NK cells, while retaining the majority of the activating receptors. NK-92™ cells do not, however, attack normal cells nor do they elicit an unacceptable immune rejection response in humans. Characterization of the NK-92™ cell line is disclosed in WO 1998/049268 and U.S. Patent Application Publication No. 2002-0068044. NK-92™ cells have been evaluated as a therapeutic agent in the treatment of certain cancers.

Vectors

Described herein are vectors for transfecting cells to produce the modified cells described herein. In one embodiment, the vectors described herein are transient expression vectors. Exogenous transgenes introduced using such vectors are not integrated in the nuclear genome of the cell; therefore, in the absence of vector replication, the foreign transgenes will be degraded or diluted over time.

In one embodiment, the vectors described herein allow for stable transfection of cells. In one embodiment, the vector allows incorporation of the transgene(s) into the genome of the cell. In one embodiment, the vectors have a positive selection marker. Positive selection markers include any genes that allow the cell to grow under conditions that would kill a cell not expressing the gene. Non-limiting examples include antibiotic resistance, e.g. geneticin (Neo gene from Tn5).

In one embodiment, the vector is a plasmid vector. In one embodiment, the vector is a viral vector. As would be understood by one of skill in the art, any suitable vector can be used. Suitable vectors are well-known in the art.

In some embodiments, the cells are transfected with mRNA encoding the protein of interest (e.g., a CAR). Transfection of mRNA results in transient expression of the protein. In one embodiment, transfection of mRNA into NK-92™ cells is performed immediately prior to administration of the cells. In one embodiment, "immediately prior" to administration of the cells refers to between about 15 minutes and about 48 hours prior to administration. Preferably, mRNA transfection is performed about 5 hours to about 24 hours prior to administration.

PD-L1

Programmed death-ligand (PD-L1) is an inhibitory ligand that binds to PD-1 to suppress T cell activation. PD-L1 is constitutively expressed and induced in tumor cells. PD-L1 is also expressed in MDSCs. It has been reported that the number of PD-L1-expressing MDSCs increased significantly in tumor-bearing mice as compared to tumor free mice, and that PD-L1 expression is significantly higher in tumor-infiltrating MDSCs as compared to those in lymphoid organs. See, Lu et al., J. Immunol., May 1, 2017, 198 (1 Supplement) 124.9. PD-L1 is also expressed in tumor-associated macrophages (TAMs) and that TAM expression of PD-L1 can directly induce T cell apoptosis after binding its receptor. Kuang et al., J. Exp. Med. 2009; 206:1327-1337.

CARs

Phenotypic changes distinguishing a tumor cell from normal cells derived from the same tissue are often associated with one or more changes in the expression of specific gene products, including the loss of normal cell surface components or the gain of others (i.e., antigens not detectable in corresponding normal, non-cancerous tissue). The antigens which are expressed in neoplastic or tumor cells, but not in normal cells, or which are expressed in neoplastic cells at levels substantially above those found in normal cells, have been termed "tumor-specific antigens" or "tumor-associated antigens." Tumor-specific antigens have been used as targets for cancer immunotherapies. One such therapy utilizes chimeric antigen receptors (CARs) expressed on the surface of immune cells, including T cells and NK cells, to improve cytotoxicity against cancer cells. CARs comprise a single-chain variable fragment (scFv) linked to at least one intracellular signaling domain. The scFv recognizes and binds an antigen on the target cell (e.g., a cancer cell) and triggers effector cell activation. The signaling domains contain immunoreceptor tyrosine-based activation domains (ITAMs) that are important for intracellular signaling by the receptor.

The present disclosure provides NK-92™ cells that have been engineered to express at least a chimeric antigen receptor (CAR) on the cell surface. CARs combine an extracellular antigen-recognizing part (usually derived from the variable domain of a specific antibody to an intracellular signaling domain (either single or with additional co-stimulatory elements) that can trigger a cytolytic response once a specific antigen is recognized. There are multiple types of CARs, which all can be used in the application. The first generation of CARs contains one cytoplasmic signaling domain. The signaling domain can be from e.g., the Fc epsilon receptor gamma (FcεRIγ) which contains one ITAM, or from CD3ζ, which contains three ITAMs. It is believed that CD3ζ CARs are more efficient at tumor eradication than FcεRIγ CARs. See, e.g., Haynes, et al. 2001, J. Immunology 166:182-187; Cartellieri, et al. 2010, J. Biomed and Biotech, Vol. 2010, Article ID 956304. The second and third generation CARs combine multiple signaling domains, e.g., the cytoplasmic signaling domain of CD3ζ and costimulatory signaling domains, such as CD28/CD134/CD137/ICOS and CD28/CD134 to a single CAR to promote the activation and proliferation of the NK-92™ cells. Thus, in some embodiments, the PD-L1 CAR expressed by the PD-L1 t-haNK cells comprises a hinge region from CD8, and/or a transmembrane domain of CD28. In some embodiments, the PD-L1 CAR comprises a cytoplasmic signaling domain of FcεRIγ. In some embodiments, the PD-L1 CAR comprises the cytoplasmic signaling domain of CD3ζ. Examples of the hinge region, the transmembrane domain of CD28 and the cytoplasmic signaling domain of FcεRIγ or CD3ζ are disclosed in U.S. Provisional application No. 62/674,936, the entire content of which is herein incorporated by reference. While prior publications such as Haynes, et al. 2001, J. Immunology 166:182-187 and Cartellieri, et al. 2010, J. Biomed and Biotech, Vol. 2010, Article ID 956304, had disclosed that CD3ζ CARs may be more efficient at tumor eradication than FcεRIγ CARs, in this case, the inventors have surprisingly and unexpectedly found that such is not the case for the cells, compositions, and methods disclosed herein. In fact, the inventors found that NK-92 cells expressing a first-generation CAR comprising an intracellular domain from FcεRIγ, which has only one ITAM domain, have equal or higher cytotoxic activity against cancer cells expressing the antigen recognized by the CAR than NK-92 cells expressing CARs with a CD3ζ signaling domain, which has three ITAM domains, even where these ITAM domains were combined with other signaling domains (i.e., second or third generation CARs; data not shown here). Exemplary CARs are schematically illustrated in FIG. 1. Notably, the IgE receptor (FcεRI) in its native context includes two gamma chains coupled to each other via a disulfide bond and is normally expressed only in eosinophils, basophils, and epidermal Langerhans cells. The inventors also made the unexpected finding that a CAR comprising an intracellular domain from FcεRIγ was expressed at higher levels on the surface of NK-92 cells than other CARs, especially those comprising the CD3ζ signaling domain.

Optionally, the CAR is specific for PD-L1. In some embodiments, PD-L1 is a human PD-L1. In some embodiments, the PD-L1 CAR comprises an amino acid sequence set forth as SEQ ID NO: 10. In some embodiments, the PD-L1 CAR has an amino acid sequence of SEQ ID NO: 14.

In some embodiments, the PD-L1 CAR polypeptide comprises a sequence that shares at least 90, 91, 92, 93, 94, 95, 96, 97, 98, or 99% identity to SEQ ID NO:10 or the CDR sequence portions within SEQ ID NO:10. In some embodiments, an epitope tag peptide, such as FLAG, myc, polyhistidine, or V5 can be added to the amino terminal domain of the polypeptide to assist in cell surface detection by using anti-epitope tag peptide monoclonal or polyclonal antibodies.

In examples, variant polypeptides are made using methods known in the art such as oligonucleotide-mediated (site-directed) mutagenesis, alanine scanning, and PCR mutagenesis. Site direct mutagenesis (Carter, 1986; Zoller and Smith, 1987), cassette mutagenesis, restriction selection mutagenesis (Wells et al., 1985) or other known techniques can be performed on the cloned DNA to produce CD16 variants (Ausubel, 2002; Sambrook and Russell, 2001).

In some embodiments, a polynucleotide encoding a PD-L1 CAR is mutated to alter the amino acid sequence encoding for CAR without altering the function of the CAR. For example, polynucleotide substitutions leading to amino acid substitutions at "non-essential" amino acid residues can be made in SEQ ID NO:9, which is a codon-optimized sequence encoding the scFv portion of the PD-L1 CAR.

Conservative substitutions in SEQ ID NO:9 whereby an amino acid of one class is replaced with another amino acid of the same class, fall within the scope of the disclosed variants as long as the substitution does not materially alter the activity of the polypeptide. Conservative substitutions are well known to one of skill in the art. Non-conservative substitutions that affect (1) the structure of the polypeptide backbone, such as a β-sheet or α-helical conformation, (2) the charge, (3) the hydrophobicity, or (4) the bulk of the side chain of the target site can modify polypeptide function or immunological identity. Non-conservative substitutions entail exchanging a member of one of these classes for another class. Substitutions may be introduced into conservative substitution sites or more preferably into non-conserved sites.

In examples, variant polypeptides are produced using methods known in the art such as oligonucleotide-mediated (site-directed) mutagenesis, alanine scanning, and PCR mutagenesis. Site direct mutagenesis (Carter, 1986; Zoller and Smith, 1987), cassette mutagenesis, restriction selection mutagenesis (Wells et al., 1985) or other known techniques can be performed on the cloned DNA to produce variants (Ausubel, 2002; Sambrook and Russell, 2001).

Optionally, the PD-L1 t-haNK cells can be used to treat cancer, in particular, a cancer that express PD-L1. Optionally, the cancer is selected from the group consisting of leukemia (including acute leukemias (e.g., acute lymphocytic leukemia, acute myelocytic leukemia (including myeloblastic, promyelocytic, myelomonocytic, monocytic, and erythroleukemia)) and chronic leukemias (e.g., chronic myelocytic (granulocytic) leukemia and chronic lymphocytic leukemia), polycythemia vera, lymphomas (e.g., Hodgkin's disease and non-Hodgkin's disease), multiple myeloma, Waldenstrom's macroglobulinemia, heavy chain disease, solid tumors including, but not limited to, sarcomas and carcinomas such as fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilm's tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, menangioma, melanoma, neuroblastoma and retinoblastoma.

Fc Receptors

In some embodiments, the NK-92™ cells are modified to express at least one Fc receptor, such that the at least one Fc receptor is displayed on the cell surface of the NK-92™ cell. Fc receptors bind to the Fc portion of antibodies. Several Fc receptors are known, and differ according to their preferred ligand, affinity, expression, and effect following binding to the antibody.

TABLE 1

Illustrative Fc receptors

| Receptor name | Principal antibody ligand | Affinity for ligand | Cell distribution | Effect following binding to antibody |
|---|---|---|---|---|
| FcγRI (CD64) | IgG1 and IgG3 | High ($Kd \sim 10^{-9}M$) | Macrophages Neutrophils Eosinophils Dendritic cells | Phagocytosis Cell activation Activation of respiratory burst Induction of microbe killing |
| FcγRIIA (CD32) | IgG | Low ($Kd > 10^{-7}M$) | Macrophages Neutrophils Eosinophils Platelets Langerhans cells | Phagocytosis Degranulation (eosinophils) |
| FcγRIIB1 (CD32) | IgG | Low ($Kd > 10^{-7}M$) | B Cells Mast cells | No phagocytosis Inhibition of cell activity |
| FcγRIIB2 (CD32) | IgG | Low ($Kd > 10^{-7}M$) | Macrophages Neutrophils Eosinophils | Phagocytosis Inhibition of cell activity |
| FcγRIIIA (CD16a) | IgG | Low ($Kd > 10^{-6}M$) | NK cells Macrophages (certain tissues) | Induction of antibody-dependent cell-mediated cytotoxicity (ADCC) Induction of cytokine release by macrophages |
| FcγRIIIB (CD16b) | IgG | Low ($Kd > 10^{-6}M$) | Eosinophils Macrophages Neutrophils Mast cells Follicular dendritic cells | Induction of microbe killing |
| FcεRI | IgE | High ($Kd \sim 10^{-10}M$) | Mast cells Eosinophils Basophils Langerhans cells Monocytes | Degranulation Phagocytosis |
| FcεRII (CD23) | IgE | Low ($Kd > 10^{-7}M$) | B cells Eosinophils Langerhans cells | Possible adhesion molecule IgE transport across human intestinal epithelium Positive-feedback mechanism to enhance allergic sensitization (B cells) |

TABLE 1-continued

Illustrative Fc receptors

| Receptor name | Principal antibody ligand | Affinity for ligand | Cell distribution | Effect following binding to antibody |
|---|---|---|---|---|
| FcαRI (CD89) | IgA | Low (Kd > 10$^{-6}$M) | Monocytes Macrophages Neutrophils Eosinophils | Phagocytosis Induction of microbe killing |
| Fcα/μR | IgA and IgM | High for IgM, Mid for IgA | B cells Mesangial cells Macrophages | Endocytosis Induction of microbe killing |
| FcRn | IgG | | Monocytes Macrophages Dendritic cells Epithelial cells Endothelial cells Hepatocytes | Transfers IgG from a mother to fetus through the placenta Transfers IgG from a mother to infant in milk Protects IgG from degradation |

In some embodiments NK-92™ cells are modified to express an Fc receptor protein on the cell surface.

In some embodiments, the Fc receptor is CD16. For purposes of this disclosure, specific amino acid residues of CD16 are designated with reference to SEQ ID NO:2, or to SEQ ID NO:1, which differs at one position relative to SEQ ID NO:2. Thus, an amino acid residue "at position 158" of a CD16 polypeptide is the amino acid residue that corresponds to position 158 of SEQ ID NO:2 (or SEQ ID NO:1), when the CD16 polypeptide and SEQ ID NO:2 are maximally aligned. In some embodiments, NK-92™ cells are modified to express a human CD16 that has a phenylalanine at position 158 of the mature form of the protein, e.g., SEQ ID NO:1. In typical embodiments, NK-92™ cells are modified to express a high affinity form of human CD16 having a valine at position 158 of the mature form of the protein, e.g., SEQ ID NO:2. Position 158 of the mature protein corresponds to position 176 of the CD16 sequence that includes the native signal peptide. In some embodiments, a CD16 polypeptide is encoded by a polynucleotide that encodes the precursor (i.e., has a native signal peptide) polypeptide sequence of SEQ ID NO:3 or of SEQ ID NO:4. Thus, in one embodiment, the Fc receptor comprises FcγRIII-A (CD16). In some embodiments, the NK-92™ cells are genetically modified to express an Fc receptor encoding a polypeptide having at least 90% sequence identity with SEQ ID NO:1 (FcγRIII-A or CD16 having a phenylalanine at position 158 (F-158); or at least 90% identity to SEQ ID NO:2 (CD16 having a valine at position 158 (F158V), higher affinity form).

In some embodiments, a polynucleotide encoding a CD16 polypeptide has at least about 70% polynucleotide sequence identity with a polynucleotide sequence encoding a full-length, including signal peptide, naturally occurring CD16 that has a phenylalanine at position 176 of the full-length CD16 (which corresponds to position 158 of the mature CD16 protein). In some embodiments, a polynucleotide encoding a CD16 polypeptide has at least about 70% polynucleotide sequence identity with a polynucleotide sequence encoding a full-length, including the signal peptide, naturally occurring CD16 that has a valine at position 176 (which corresponds to position 158 of the mature protein). In some embodiments, a polynucleotide encoding CD16 has at least 70%, 80%, 90%, or 95% identity to SEQ ID NO:5 and comprises a codon encoding valine at the position of the polynucleotide that encodes position 176 of the full-length, including the signal peptide, CD16 polypeptide. In some embodiments, a polynucleotide encoding CD16 comprises SEQ ID NO:5, but with a codon encoding valine at position 176 of the full-length CD16.

In some embodiments, the CD16 polynucleotide encodes a polypeptide having at least 70%, 80%, 90%, or 95% identity to SEQ ID NO:1 or SEQ ID NO:2. In some embodiments, the polynucleotide encodes a polypeptide having at least 70% 80%, 90%, or 95% identity to SEQ ID NO:2 and comprises a valine at position 158 as determined with reference to SEQ ID NO:2. In some embodiments the polynucleotide encodes SEQ ID NO:2. In some embodiments, a CD16 polynucleotide encodes an extracellular domain of CD16 with or without the signal sequence, or any other fragment of a full length CD16, or a chimeric receptor encompassing at least partial sequence of CD16 fused to an amino acid sequence of another protein. In other embodiments, an epitope tag peptide, such as FLAG, myc, polyhistidine, or V5 can be added to the amino terminal domain of the mature polypeptide to assist in cell surface detection by using anti-epitope tag peptide monoclonal or polyclonal antibodies.

In some embodiments, homologous CD16 polynucleotides may be about 150 to about 700, about 750, or about 800 polynucleotides in length, although CD16 variants having more than 700 to 800 polynucleotides are within the scope of the disclosure.

Homologous polynucleotide sequences include those that encode polypeptide sequences coding for variants of CD16. Homologous polynucleotide sequences also include naturally occurring allelic variations related to SEQ ID NO:1. Transfection of an NK-92™ cell with any polynucleotide encoding a polypeptide having the amino acid sequence shown in either SEQ ID. NO: 1 or SEQ ID NO: 2, a naturally occurring variant thereof, or a sequence that is at least 70% identical, or at least 80%, 90%, or 95% identical to SEQ ID. NO: 1 or SEQ ID NO: 2 is within the scope of the disclosure. In some embodiments, homologous polynucleotide sequences encode conservative amino acid substitutions in SEQ ID. NO: 1 or SEQ ID NO: 2. In some embodiments, NK-92™ cells are transfected using a degenerate homologous CD16 polynucleotide sequence that differs from a native polynucleotide sequence, but encodes the same polypeptide.

In other examples, cDNA sequences having polymorphisms that change the CD16 amino acid sequences are used to modify the NK-92™ cells, such as, for example, the allelic variations among individuals that exhibit genetic polymorphisms in CD16 genes. In other examples, CD16 genes from other species that have a polynucleotide sequence that differs from the sequence of SEQ ID NO:1 are used to modify NK-92™ cells.

Variant polypeptides can be made using methods known in the art such as oligonucleotide-mediated (site-directed) mutagenesis, alanine scanning, and PCR mutagenesis. Site direct mutagenesis (Carter, 1986; Zoller and Smith, 1987), cassette mutagenesis, restriction selection mutagenesis (Wells et al., 1985) or other known techniques can be performed on the cloned DNA to produce CD16 variants (Ausubel, 2002; Sambrook and Russell, 2001).

In some embodiments, a polynucleotide encoding a CD16 is mutated to alter the amino acid sequence encoding for CD16 without altering the function of CD16. For example, polynucleotide substitutions leading to amino acid substitutions at "non-essential" amino acid residues can be made in SEQ ID NO:1 or SEQ ID NO:2.

Conservative substitutions in SEQ ID. NO:1 or SEQ ID NO:2, whereby an amino acid of one class is replaced with another amino acid of the same class, fall within the scope of the disclosed CD16 variants as long as the substitution does not materially alter the activity of the polypeptide. Conservative substitutions are well known to one of skill in the art. Non-conservative substitutions that affect (1) the structure of the polypeptide backbone, such as a β-sheet or α-helical conformation, (2) the charge, (3) the hydrophobicity, or (4) the bulk of the side chain of the target site can modify CD16 polypeptide function or immunological identity. Non-conservative substitutions entail exchanging a member of one of these classes for another class. Substitutions may be introduced into conservative substitution sites or more preferably into non-conserved sites.

In some embodiments, CD16 polypeptide variants are at least 200 amino acids in length and have at least 70% amino acid sequence identity, or at least 80%, or at least 90% identity to SEQ ID NO:1 or SEQ ID NO:2. In some embodiments, CD16 polypeptide variants are at least 225 amino acid in length and have at least 70% amino acid sequence identity, or at least 80%, or at least 90% identity to SEQ ID NO:1 or SEQ ID NO:2. In some embodiments, CD16 polypeptide variants have a valine at position 158 as determined with reference to SEQ ID NO:2.

In some embodiments a nucleic acid encoding a CD16 polypeptide may encode a CD16 fusion protein. A CD16 fusion polypeptide includes any portion of CD16 or an entire CD16 fused with a non-CD16 polypeptide. Fusion polypeptides are conveniently created using recombinant methods. For example, a polynucleotide encoding a CD16 polypeptide such as SEQ ID NO:1 or SEQ ID NO:2 is fused in-frame with a non-CD16 encoding polynucleotide (such as a polynucleotide sequence encoding a signal peptide of a heterologous protein). In some embodiment, a fusion polypeptide may be created in which a heterologous polypeptide sequence is fused to the C-terminus of CD16 or is positioned internally in the CD16. Typically, up to about 30% of the CD16 cytoplasmic domain may be replaced. Such modification can enhance expression or enhance cytotoxicity (e.g., ADCC responsiveness). In other examples, chimeric proteins, such as domains from other lymphocyte activating receptors, including but not limited to Ig-a, Ig-B, CD3-e, CD3-d, DAP-12 and DAP-10, replace a portion of the CD16 cytoplasmic domain.

Fusion genes can be synthesized by conventional techniques, including automated DNA synthesizers and PCR amplification using anchor primers that give rise to complementary overhangs between two consecutive gene fragments that can subsequently be annealed and reamplified to generate a chimeric gene sequence (Ausubel, 2002). Many vectors are commercially available that facilitate sub-cloning CD16 in-frame to a fusion moiety.

Cytokines

The cytotoxicity of NK-92 cells is dependent on the presence of cytokines (e.g., interleukin-2 (IL-2)). The cost of using exogenously added IL-2 needed to maintain and expand NK-92 cells in commercial scale culture is significant. The administration of IL-2 to human subjects in sufficient quantity to continue activation of NK92 cells would cause adverse side effects.

In one embodiment, NK-92™ cells are modified to express at least one cytokine. In particular, the at least one cytokine is IL-2 (SEQ ID NO:6), IL-12, IL-15, IL-18, IL-21, or a variant thereof. In some embodiments, the cytokine is IL-2 or a variant thereof. In certain embodiments, the IL-2 is a variant that is targeted to the endoplasmic reticulum. In some embodiments, the cytokine is IL-15 or a variant thereof. In certain embodiments, the IL-15 is a variant that is targeted to the endoplasmic reticulum.

In one embodiment, the IL-2 is cloned and expressed with a signal sequence that directs the IL-2 to the endoplasmic reticulum (erIL-2) (SEQ ID NO: 7). This permits expression of IL-2 at levels sufficient for autocrine activation, but without releasing IL-2 extracellularly. See Konstantinidis et al "Targeting IL-2 to the endoplasmic reticulum confines autocrine growth stimulation to NK-92™ cells" *Exp Hematol.* 2005 February; 33(2):159-64. Continuous activation of the FcR-expressing NK-92 cells can be prevented, e.g., by the presence of the suicide gene.

Suicide Gene

The term "suicide gene" refers to a transgene that allows for the negative selection of cells expressing the suicide gene. A suicide gene is used as a safety system, allowing cells expressing the gene to be killed by introduction of a selective agent. This is desirable in case the recombinant gene causes a mutation leading to uncontrolled cell growth, or the cells themselves are capable of such growth. A number of suicide gene systems have been identified, including the herpes simplex virus thymidine kinase (TK) gene, the cytosine deaminase gene, the varicella-zoster virus thymidine kinase gene, the nitroreductase gene, the *Escherichia coli* gpt gene, and the *E. coli* Deo gene. Typically, the suicide gene encodes for a protein that has no ill effect on the cell but, in the presence of a specific compound, will kill the cell. Thus, the suicide gene is typically part of a system.

In one embodiment, the suicide gene is active in NK-92™ cells. In one embodiment, the suicide gene is the thymidine kinase (TK) gene. The TK gene may be a wild-type or mutant TK gene (e.g., tk30, tk75, sr39tk). Cells expressing the TK protein can be killed using ganciclovir.

In another embodiment, the suicide gene is cytosine deaminase, which is toxic to cells in the presence of 5-fluorocytosine. Garcia-Sanchez et al. "Cytosine deaminase adenoviral vector and 5-fluorocytosine selectively reduce breast cancer cells 1 million-fold when they contaminate hematopoietic cells: a potential purging method for autologous transplantation." *Blood.* 1998 Jul. 15; 92(2):672-82.

In another embodiment, the suicide gene is cytochrome P450, which is toxic in the presence of ifosfamide or cyclophosphamide. See, e.g. Touati et al. "A suicide gene therapy combining the improvement of cyclophosphamide tumor cytotoxicity and the development of an anti-tumor immune response." *Curr Gene Ther.* 2014; 14(3):236-46.

In another embodiment, the suicide gene is iCasp9. Di Stasi, (2011) "Inducible apoptosis as a safety switch for adoptive cell therapy." *N Engl J Med* 365: 1673-1683. See also Morgan, "Live and Let Die: A New Suicide Gene Therapy Moves to the Clinic" *Molecular Therapy* (2012); 20: 11-13. iCasp9 induces apoptosis in the presence of a small molecule, AP1903. AP1903 is biologically inert small molecule, that has been shown in clinical studies to be well tolerated, and has been used in the context of adoptive cell therapy.

Codon Optimization

In some embodiments, the sequence of the constructs used to transform the aNK cells are codon-optimized to maximize expression efficiency of PD-L1 CAR, CD16, and/or erIL-2 in human systems. Codon optimization is typically performed by modifying a nucleic acid sequence by replacing at least one, more than one, or a significant number, of codons in the native sequence with codons that are more frequently or most frequently used in the gene of the expression system. Codon optimization can be used to the rate of translation or to produce recombinant RNA transcripts having desirable properties, such as a longer half-life, as compared with transcripts produced using a non-optimized sequence. Methods for codon optimization are readily available, for example, GeneArt™, from Thermo Fisher Scientific (Waltham, Mass.); Optimizer, accessible free of charge at http://genomes.urv.es/OPTIMIZER, and GeneGPS® Expression Optimization Technology from DNA 2.0 (Newark, Calif.). In particular embodiments, the coding sequence for PD-L1 CAR is codon-optimized and comprises the sequence (scFv portion) as set forth in SEQ ID NO: 9, which encodes the protein sequence of SEQ ID NO:10. In some embodiments, the codon-optimized PD-L1 CAR coding sequence is the sequence set forth in SEQ ID NO: 14, which encodes the protein sequence of SEQ ID NO:15.

Transgene Expression

Transgenes can be engineered into an expression vector by any mechanism known to those of skill in the art. Where multiple transgenes are to be inserted into a cell, transgenes may be engineered into the same expression vector or a different expression vector.

In some embodiments, the cells are transfected with mRNA encoding the transgenic protein to be expressed.

Transgenes and mRNA can be introduced into the NK-92™ cells using any transfection method known in the art, including, by way of non-limiting example, infection, electroporation, lipofection, nucleofection, or "gene-gun."

NK-92™ Cells that Express a Pd-L1 CAR

This disclosure provides a modified NK-92™ cell expressing a PD-L1 CAR and a FcR. Optionally, the modified NK-92™ cell further expresses an IL-2.

In some embodiments, the modified NK-92™ cells comprises a multi-cistronic transgene and the multi-cistronic transgene encodes the chimeric antigen receptor and the Fc receptor, and optionally IL-2.

In some embodiments, the FcR is a CD16. In some embodiments, the CD16 is a high affinity CD16, which comprises or consists of SEQ ID NO:2. In some embodiments the IL-2 is erIL-2, which comprises or consists of SEQ ID NO: 7.

In some embodiments, the CAR-coding sequence and the CD16-coding sequence are separated by a P2A sequence (SEQ ID NO: 8 ggaagcggagctactaacttcagcctgctgaagcaggctggagacgtggaggagaaccctggacct). This configuration allows equimolar expression of CAR and CD16 from a single mRNA.

In some embodiments, the CD16 coding sequence and the erIL-2-coding sequence are separated by an internal ribosomal entry sequence (IRES) that allows internal translation initiation.

Figure 2:
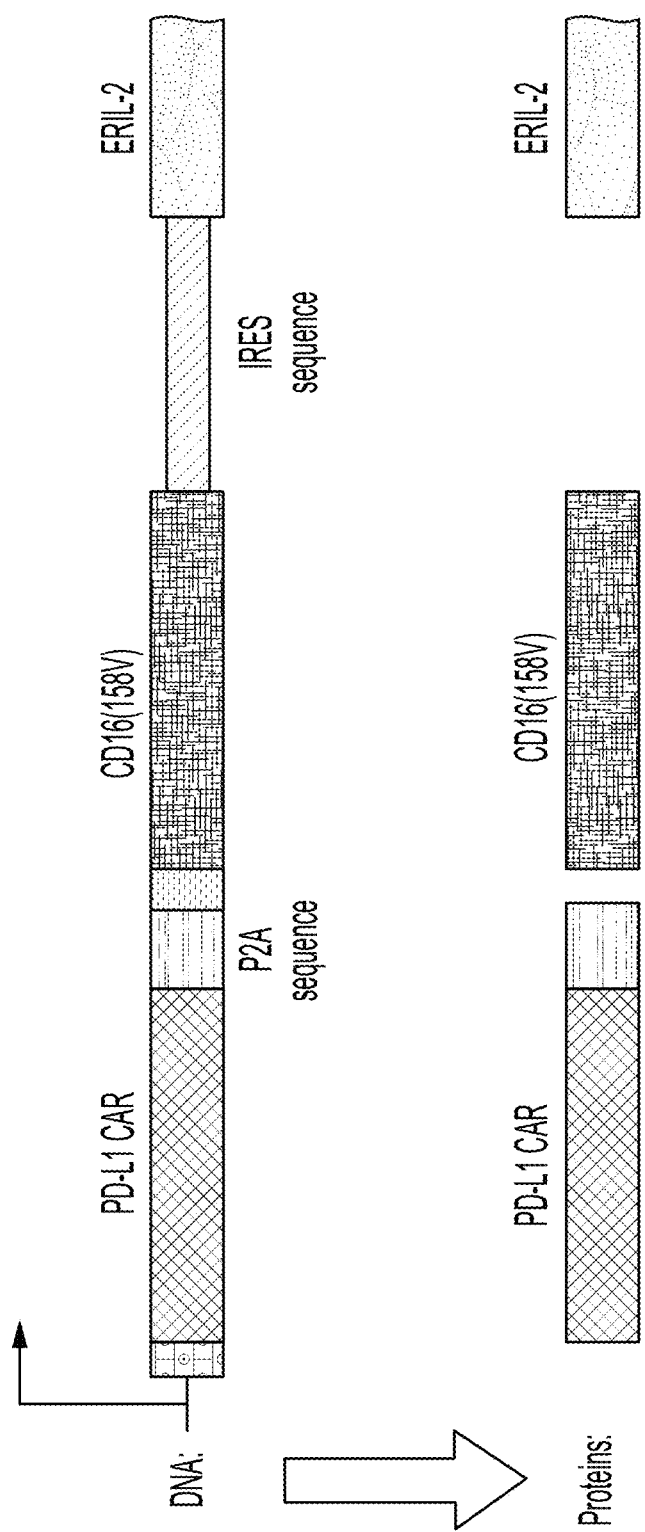
FIG. 2 shows the components of a tricistronic plasmid comprising a CAR coding sequence, a P2A sequence, a CD16 coding sequence, and an erIL-2 coding sequence.

In some embodiments, the modified NK-92™ cells comprises a tricistronic construct which expresses a CAR, a high affinity CD16, and an erIL-2 from a single mRNA. In some embodiments, the tricistronic construct comprises the sequence as set forth in SEQ ID NO: 11. The integration of the CAR enables effector cells to specifically engage and kill target cells that express a target recognized by the CAR; the integration of CD16 enables ADCC when combined with a therapeutic monoclonal antibody; and erIL2, which allows cell expansion in absence of exogenous IL-2 and maintains selective pressure for transgene expression. One illustrative tricistronic construct is shown in FIG. 2, and an exemplary protein sequence for PD-L1 CAR and CD16 fusion protein is shown in SEQ ID NO: 12.

To produce modified NK-92™ cells expressing a CAR and a CD16 (e.g., the high affinity CD16), and an erIL-2, the multi-cistronic plasmid is introduced into the aNK™ cells by, for example, electroporation. The transformed NK-92™ cells are grown in media free of IL-2, and individual clones can be selected from the transformed NK-92™ cells by limiting dilution cloning and characterized based on criteria, which include, for example, high levels of CAR and CD16 expression, cytotoxicity, ADCC, growth rate, and/or IL-2 secretion. Suitable clones may also express surface markers, e.g., CD3, CD16, CD54, CD56, NKG2D, and/or NKp30 in levels substantially similar to that of the aNK™ cells. Optionally, whole genome sequencing (WGS) are performed to determine the transgene integration site. Clones meeting one or more of these criteria can be selected for further development and used to treat patients in clinic.

Expression

Expression of IL-2 can be confirmed by the capability of the modified NK-92™ cells in IL-2 free conditions. Expression of the CAR and CD16 can be measured by flow cytometry. For NK-92™ cells that have been transformed with the tricistronic construct comprising the coding sequences of CAR, CD16, and IL-2 (e.g., erIL-2, SEQ ID NO: 13), typically at least 70%, at least 80%, at least 85% of the transformed cells that are able to grow IL-2-free conditions also show high expression levels of both CAR and CD16.

Optionally, IL-2 secretion levels of the transformed NK-92™ cells can be measured at various time points using methods well known in the art, for example, by ELISA.

In some embodiments, the IL-2 levels in the culture supernatant are measured to determine the levels of IL-2 released to the cell culture medium. In some embodiments, the IL-2 levels in the cell pellets are measured to assess total intracellular levels of IL-2. In some embodiments, both the IL-2 amount in the supernatant and the IL-2 amount in the cell pellets are measured to determine the total amount of IL-2 produced by the transformed NK-92™ cells.

Optionally, other surface markers of the transformed NK-92™ cells can be measured by flow cytometry. These markers include, but are not limited to, CD54, CD56, NKG2D, NKp30, and CD3. Suitable clones are those that have demonstrated substantially similar expression levels of these markers to those of aNK™ cells under the same growth conditions.

Cytotoxicity

Optionally, cytotoxicity of the NK-92™ cells transformed with the tricistronic plasmid can also be tested using methods well known in the art. Cytotoxicity of NK-92™ cells can be reflected by their direct cytotoxicity or ADCC activity. Direct cytotoxicity of the produced NK-92™ cells, the ability to target and kill aberrant cells, such as tumor cells, can be assessed by methods well known in the art, for example, a $^{51}$Cr release assay (Gong et al. (Leukemia, April; 8(4): 652-8 (1994)) using the procedure described by Klingemann et al. (Cancer Immunol. Immunother. 33:395-397 (1991)). In some embodiments, the target cells express an antigen that can be recognized by the CAR expressed on the surface of the t-haNK cells. Briefly, $^{51}$Cr-labeled target cells are mixed with NK-92™ cells and are lysed. The percentage of specific cytotoxicity can be calculated based on the amount of released $^{51}$Cr. See Patent Pub. No. US20020068044.

Optionally, the cytotoxicity of the NK-92® cells transformed with the tricistronic plasmid can be assessed using a flow-based in cytotoxicity assay. Effector cells (the NK-92® cells) and fluorophore-labeled target cells, e.g., tumor cells, are mixed at different effector to target ratios. Propidium Iodide (PI) can be added to the cells and samples can be analyzed a flow cytometer. Preferably the fluorophore that is used to label the target cells can be distinguished from PI by in a flow cytometer. In some embodiments, the fluorophore is CFSE. In some embodiments, the fluorophore is PKHGL67. The cytotoxicity can be determined by the % of PI-positive cells within the fluorophore-positive target population.

Alternatively, direct cytotoxicity of the produced NK-92™ cells can also be assessed using a calcein release assay. For example, the NK-92™ cells (referred to as the effector in the assay) can be mixed with the calcein loaded target cells (referred to as target in the assay) at certain ratios. After incubation for a period of time, the calcein released from the target cells can be assessed, e.g., by a fluorescence plate reader. The ratio of the effector and target used in the assay may vary, optionally the effector:target ratio may be 20:1, 15:1, 10:1, 8:1, or 5:1; preferably the effector:target ratio is 10:1. The target cells can be any cells that express an antigen molecule that can be recognized by the CAR on the NK-92™ cells (t-haNK cells). For example, MDA MB 231 cells can be recognized by the PD-L1 CAR and are target cells for PD-L1 t-haNK cells. The values of cytotoxicity of NK-92™ cells may vary depending on the type of target cells used as well as the effector:target ratio. In general, the NK-92™ cells produced using the methods described herein can have a cytotoxicity of 60-100%, e.g., 70-100% or 80-100%. In some cases, the NK-92™ cells may have a cytotoxicity of 80-100%, e.g., 82-100%, 85-100%, 87-100%, 88-100%, or 89-100%, by a calcein release assay when using an effector:target ratio of 1:10.

Optionally, the cytotoxicity of NK-92™ cells, e.g., t-haNK cells, that is assessed is the antibody dependent cytotoxicity (ADCC). Methods for measuring the ADCC activity of NK-92™ cells are similar to the methods of measuring direct cytotoxicity as described above except that an antibody that can recognize the target cell is also added. The Fc receptor of the NK cells recognizes the cell-bound antibodies and triggers cytolytic reaction and killing the target cells. In one illustrative example, the t-haNK cells can be incubated with Herceptin (an anti-Her2 antibody) and SKBr3 (target cells) and killing of the SKBr3 cells can be measured by the release of internal components of the target cells, e.g., $^{51}$Cr or calcein, as described above.

Doubling Time

The growth rate of the NK-92™ cells, e.g., t-haNK cells, can be assessed using cell doubling time, i.e., the time it takes for the cells to proliferate to reach twice the initial cell number. The doubling time is reversely related to the growth rate of the NK-92™ cells; the greater the doubling time, the lower the growth rate.

WGS

Optionally, whole genome sequencing (WGS) of the modified NK-92™ cells are performed to identify the insertion site of the multi-cistronic construct.

Therapeutic Applications

This disclosure also provides a method to treat any type of cancer in a subject at any stage of the disease. Non-limiting examples of the suitable cancers include carcinoma, melanoma, or sarcoma. In some embodiments, the invention is used to treat cancer of hemopoietic origin such as leukemia or lymphoma. In some embodiments, the cancer is a solid tumor.

In some embodiments, the method to treat any type of cancer in a subject comprises administering to the patient a therapeutically effective amount of the NK-92™ cells as described above, wherein the thereby treating cancer. In some embodiments, the NK-92™ cells express a Fc receptor, e.g., a high affinity Fc receptor that has the sequence set forth in SEQ ID NO:2. In some embodiments, the NK-92™ cells express a PD-L1 CAR, a Fc receptor and an IL-2. In some embodiments, the modified NK-92™ cells comprise a multi-cistronic construct and wherein the multi-cistronic construct encodes the chimeric antigen receptor and the Fc receptor.

Also provided are methods of treating a subject in need thereof with the modified NK-92™ cells as described herein. In some embodiments, the subject or patient is suffering from cancer or an infectious disease, such as a viral infection.

The modified NK-92™ cells can be administered to an individual by absolute numbers of cells, e.g., said individual can be administered from about 1000 cells/injection to up to about 10 billion cells/injection, such as at about, at least about, or at most about, $1\times10^8$, $1\times10^7$, $5\times10^7$, $1\times10^6$, $5\times10^6$, $1\times10^5$, $5\times10^5$, $1\times10^4$, $5\times10^4$, $1\times10^3$, $5\times10^3$ (and so forth) NK-92™ cells per injection, or any ranges between any two of the numbers, end points inclusive. Therefore, this disclosure also provides a composition comprising a plurality of NK-92™ cells, wherein the number of cells are $1\times10^8$, $1\times10^7$, $5\times10^7$, $1\times10^6$, $5\times10^6$, $1\times10^5$, $5\times10^5$, $1\times10^4$, $5\times10^4$, $1\times10^3$, or $5\times10^3$ (and so forth).

In other embodiments, said individual can be administered from about 1000 cells/injection/$m^2$ to up to about 10 billion cells/injection/$m^2$, such as at about, at least about, or at most about, $1\times10^8/m^2$, $1\times10^7/m^2$, $5\times10^7/m^2$, $1\times10^6/m^2$, $5\times10^6/m^2$, $1\times10^5/m^2$, $5\times10^5/m^2$, $1\times10^4/m^2$, $5\times10^4/m^2$, $1\times10^3/m^2$, $5\times10^3/m^2$ (and so forth) NK-92™ cells per injection, or any ranges between any two of the numbers, end points inclusive.

In other embodiments, NK-92™ cells can be administered to such individual by relative numbers of cells, e.g., said individual can be administered about 1000 cells to up to about 10 billion cells per kilogram of the individual, such as at about, at least about, or at most about, $1\times10^8$, $1\times10^7$, $5\times10^7$, $1\times10^6$, $5\times10^6$, $1\times10^5$, $5\times10^5$, $1\times10^4$, $5\times10^4$, $1\times10^3$, or $5\times10^3$ (and so forth) NK-92™ cells per kilogram of the individual, or any ranges between any two of the numbers, end points inclusive.

In other embodiments, the total dose may be calculated by $m^2$ of body surface area, including about $1\times10^{11}$, $1\times10^{10}$, $1\times10^9$, $1\times10^8$, $1\times10^7$, per $m^2$, or any ranges between any two of the numbers, end points inclusive. The average person is about 1.6 to about 1.8 $m^2$. In a preferred embodiment, between about 1 billion and about 3 billion NK-92™ cells are administered to a patient. In other embodiments, the amount of NK-92™ cells injected per dose may be calculated by m² of body surface area, including $1\times10^{11}$, $1\times10^{10}$, $1\times10^9$, $1\times10^8$, $1\times10^7$, per m². The average body surface area for a person is 1.6-1.8 m².

In other embodiments, NK-92™ cells can be administered to such individual by relative numbers of cells, e.g., said individual can be administered about 1000 cells to up to about 10 billion cells per kilogram of the individual, such as at about, at least about, or at most about, $1\times10^8$, $1\times10^7$, $5\times10^7$, $1\times10^6$, $5\times10^6$, $1\times10^5$, $5\times10^5$, $1\times10^4$, $5\times10^4$, $1\times10^3$, or $5\times10^3$ (and so forth) NK-92™ cells per kilogram of the individual, or any ranges between any two of the numbers, end points inclusive.

NK-92™ cells can be administered once to a patient with cancer or they can be administered multiple times, e.g., once every 1, 2, 3, 4, 5, 6, 7, 8, 9, 10, 11, 12, 13, 14, 15, 16, 17, 18, 19, 20, 21, 22 or 23 hours, or once every 1, 2, 3, 4, 5, 6 or 7 days, or once every 1, 2, 3, 4, 5, 6, 7, 8, 9, 10 or more weeks during therapy, or any ranges between any two of the numbers, end points inclusive.

In some embodiments, NK-92™ cells are administered in a composition comprising the NK-92™ cells and a medium, such as human serum or an equivalent thereof. In some embodiments, the medium comprises human serum albumin. In some embodiments, the medium comprises human plasma. In some embodiments, the medium comprises about 1% to about 15% human serum or human serum equivalent. In some embodiments, the medium comprises about 1% to about 10% human serum or human serum equivalent. In some embodiments, the medium comprises about 1% to about 5% human serum or human serum equivalent. In a preferred embodiment, the medium comprises about 2.5% human serum or human serum equivalent. In some embodiments, the serum is human AB serum. In some embodiments, a serum substitute that is acceptable for use in human therapeutics is used instead of human serum. Such serum substitutes may be known in the art, or developed in the future. Although concentrations of human serum over 15% can be used, it is contemplated that concentrations greater than about 5% will be cost-prohibitive. In some embodiments, NK-92™ cells are administered in a composition comprising NK-92™ cells and an isotonic liquid solution that supports cell viability. In some embodiments, NK-92™ cells are administered in a composition that has been reconstituted from a cryopreserved sample.

Pharmaceutically acceptable compositions comprising the NK-92™ cells can include a variety of carriers and excipients. A variety of aqueous carriers can be used, e.g., buffered saline and the like. These solutions are sterile and generally free of undesirable matter. Suitable carriers and excipients and their formulations are described in Remington: The Science and Practice of Pharmacy, 21st Edition, David B. Troy, ed., Lippicott Williams & Wilkins (2005). By pharmaceutically acceptable carrier is meant a material that is not biologically or otherwise undesirable, i.e., the material is administered to a subject without causing undesirable biological effects or interacting in a deleterious manner with the other components of the pharmaceutical composition in which it is contained. If administered to a subject, the carrier is optionally selected to minimize degradation of the active ingredient and to minimize adverse side effects in the subject. As used herein, the term pharmaceutically acceptable is used synonymously with physiologically acceptable and pharmacologically acceptable. A pharmaceutical composition will generally comprise agents for buffering and preservation in storage and can include buffers and carriers for appropriate delivery, depending on the route of administration.

These compositions for use in in vivo or in vitro may be sterilized by sterilization techniques employed for cells. The compositions may contain acceptable auxiliary substances as required to approximate physiological conditions such as pH adjusting and buffering agents, toxicity adjusting agents and the like, for example, sodium acetate, sodium chloride, potassium chloride, calcium chloride, sodium lactate and the like. The concentration of cells in these formulations and/or other agents can vary and will be selected primarily based on fluid volumes, viscosities, body weight and the like in accordance with the particular mode of administration selected and the subject's needs.

In one embodiment, NK-92™ cells are administered to the patient in conjunction with one or more other treatments or agent for the cancer being treated. In some embodiments, the one or more other treatments for the cancer being treated include, for example, an antibody, radiation, chemotherapeutic, stem cell transplantation, or hormone therapy.

In some embodiments, NK-92™ cells and the other cancer agent/treatment are administered simultaneously or approximately simultaneously (e.g., within about 1, 5, 10, 15, 20, or 30 minutes of each other). In some embodiments, the NK-92™ cells and the other cancer agent/treatment are administered sequentially. In some embodiments, the other cancer treatment/agent is administered one, two, or three days after the administration of the NK-92™ cells.

In one embodiment, the other cancer agent is an antibody. In one embodiment, NK-92™ cells are administered in conjunction with an antibody targeting the diseased cells. In one embodiment, NK-92™ cells and an antibody are administered to the patient together, e.g., in the same formulation; separately, e.g., in separate formulations, concurrently; or can be administered separately, e.g., on different dosing schedules or at different times of the day. When administered separately, the antibody can be administered via any suitable route, such as intravenous or intra-tumoral injection.

In some embodiments, NK-92™ cells of the present disclosure are used in combination with therapeutic antibodies and/or other anti-cancer agents. Therapeutic antibodies may be used to target cells that express cancer-associated or tumor-associated markers. Examples of cancer therapeutic monoclonal antibodies are shown in Table 4. In some embodiments, the NK-92™ cells express a Fc receptor, e.g., a high affinity Fc receptor that has the sequence set forth in SEQ ID NO:2. In some embodiments, the NK-92™ cells are haNK® cells. In one embodiment, the therapeutic antibody is avelumab.

TABLE 2

Illustrative therapeutic monoclonal antibodies
Examples of FDA-approved therapeutic monoclonal antibodies

| Antibody | Brand name | Company | Target | Indication (Targeted disease) |
|---|---|---|---|---|
| Alemtuzumab | Campath ® | Genzyme | CD52 | Chronic lymphocytic leukemia |
| Brentuximab vedotin | Adcetris ® | | CD30 | Anaplastic large cell lymphoma (ALCL) and Hodgkin lymphoma |

TABLE 2-continued

Illustrative therapeutic monoclonal antibodies
Examples of FDA-approved therapeutic monoclonal antibodies

| Antibody | Brand name | Company | Target | Indication (Targeted disease) |
|---|---|---|---|---|
| Cetuximab | Erbitux® | Bristol-Myers Squibb/Eli Lilly/Merck KGaA | epidermal growth factor receptor | Colorectal cancer, Head and neck cancer |
| Gemtuzumab | Mylotarg® | Wyeth | CD33 | Acute myelogenous leukemia (with calicheamicin) |
| Ibritumomab tiuxetan | Zevalin® | Spectrum Pharmaceuticals, Inc. | CD20 | Non-Hodgkin lymphoma (with yttrium-90 or indium-111) |
| Ipilimumab (MDX-101) | Yervoy® | | blocks CTLA-4 | Melanoma |
| Ofatumumab | Arzerra® | | CD20 | Chronic lymphocytic leukemia |
| Palivizumab | Synagis® | MedImmune | an epitope of the RSV F protein | Respiratory Syncytial Virus |
| Panitumumab | Vectibix® | Amgen | epidermal growth factor receptor | Colorectal cancer |
| Rituximab | Rituxan® Mabthera® | Biogen Idec/Genentech | CD20 | Non-Hodgkin lymphoma |
| Tositumomab | Bexxar® | GlaxoSmithKline | CD20 | Non-Hodgkin lymphoma |
| Trastuzumab | Herceptin® | Genentech | ErbB2 | Breast cancer |
| Blinatunomab | | | bispecific CD19-directed CD3 T-cell engager | Philadelphia chromosome-negative relapsed or refractory B cell precursor acute lymphoblastic leukemia (ALL) |
| Avelumab | Bavencio® | Merck KGaA and Pfizer and Eli Lilly | anti-PD-L1 | Non-small cell lung cancer, metastatic Merkel cell carcinoma; gastic cancer, breast cancer, ovarian cancer, bladder cancer, melanoma, meothelioma, including metastatic or locally advanced solid tumors |
| Daratumumab | | | CD38 | Multiple myeloma |
| Elotuzumab | | | a SLAMF7-directed (also known as CD319) immunostimulatory antibody | Multiple myeloma |

Administration of such NK-92™ cells may be carried out simultaneously with the administration of the monoclonal antibody, or in a sequential manner. In some embodiments, the NK-92™ cells are administered to the subject after the subject has been treated with the monoclonal antibody. Alternatively, the NK-92™ cells may be administered at the same time, e.g., within 24 hours, of the monoclonal antibody.

In some embodiments, NK-92™ cells are administered intravenously. In some embodiments the NK-92™ cells are infused directly into the bone marrow.

Therefore, this disclosure provides a method of treating cancer or viral infection in a patient in need thereof, the method comprising administering to the patient a therapeutically effective amount of the NK-92™ cells disclosed herein to thereby treating cancer.

Kits

Also disclosed are kits for the treatment of cancer or an infectious disease using compositions comprising a plurality of NK-92™ cells as described herein. In some embodiments, the kits of the present disclosure may also include at least one monoclonal antibody. The NK-92™ cell included in the kit expresses a CAR and a Fc receptor. In some embodiments, the NK-92™ cell further expresses an IL-2, e.g., an erIL-2, or IL-15, e.g., an erIL-15. In some embodiments, the NK-92™ cell comprises a multi-cistronic construct and wherein the multi-cistronic construct encodes the chimeric antigen receptor, the Fc receptor, and optionally IL-2 or IL-15.

In certain embodiments, the kit may contain additional compounds such as therapeutically active compounds or drugs that are to be administered before, at the same time or after administration of NK-92™ cells. Examples of such compounds include an antibody, vitamins, minerals, fludrocortisone, ibuprofen, lidocaine, quinidine, chemotherapeutic, etc.

In various embodiments, instructions for use of the kits will include directions to use the kit components in the treatment of a cancer or an infectious disease. The instructions may further contain information regarding how to handle the NK-92™ cells (e.g., thawing and/or culturing). The instructions may further include guidance regarding the dosage and frequency of administration.

In certain embodiments, the kit further comprises one or more containers filled with one or more compositions described herein, e.g., a composition comprising NK-92™ cells as described herein. Optionally associated with such containers can be a label indicating the kit is for treating a cancer, such as those described herein. Optionally the label also includes a notice in the form prescribed by a governmental agency regulating the manufacture, use or sale of pharmaceuticals or biological products, which notice reflects approval by the agency of manufacture, use or sale for human administration.

Disclosed are materials, compositions, and components that can be used for, can be used in conjunction with, can be used in preparation for, or are products of the disclosed methods and compositions. These and other materials are disclosed herein, and it is understood that when combinations, subsets, interactions, groups, etc. of these materials are disclosed that while specific reference of each various individual and collective combinations and permutations of these compounds may not be explicitly disclosed, each is specifically contemplated and described herein. For example, if a method is disclosed and discussed and a number of modifications that can be made to a number of molecules including the method are discussed, each and every combination and permutation of the method, and the modifications that are possible are specifically contemplated unless specifically indicated to the contrary. Likewise, any subset or combination of these is also specifically contemplated and disclosed. This concept applies to all aspects of this disclosure including, but not limited to, steps in methods using the disclosed compositions. Thus, if there are a variety of additional steps that can be performed, it is understood that each of these additional steps can be performed with any specific method steps or combination of method steps of the disclosed methods, and that each such combination or subset of combinations is specifically contemplated and should be considered disclosed.

EXAMPLES

The following examples are for illustrative purposes only and should not be interpreted as limitations. There are a variety of alternative techniques and procedures available to those of skill in the art which would similarly permit one to successfully perform the examples below.

Example 1: Producing the PD-L1 CAR Modified NK-92™ Cells

PD-L1 CAR was cloned into a bicistronic plasmid pNEUKv1 FcR_IL-2 vector that also contained CD16 and erIL-2 transgenes. The tricistronic plasmids were electroporated into the aNK™ cells. The PD-L1 CAR-expressing NK-92™ cells were selected by IL-2-depleted media because untransformed aNK™ cells, being IL-2 dependent, could not survive in IL-2 depleted media.
Limiting Dilution Cloning An aliquot of a polyclonal PD-L1 t-haNK pool culture diluted to a density of 1.5 cells/ml in growth medium without IL-2 supplementation. This cell suspension was aliquoted in 96-well plates at a volume of 200 µl per well, corresponding to 0.3 cells per well on average. The plates were incubated at 37° C. for 10 days, then visually checked for cell growth. Growing cultures, now named clones, were picked and transferred to larger vessels for further expansion and characterization.

Example 2: Phenotypes of the Modified NK-92™ Cells

Figure 3:
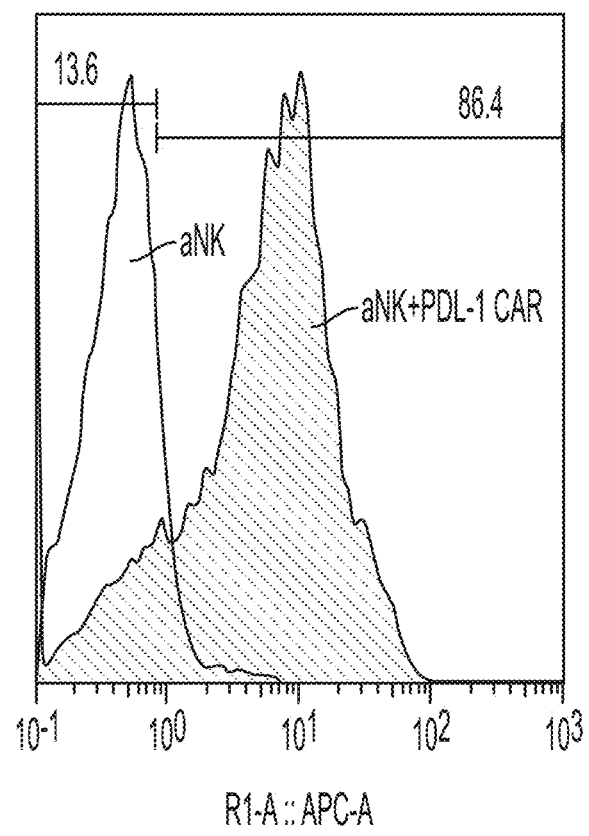
FIG. 3 shows results of flow cytometric analysis of the expression of PD-L1-CAR on modified NK-92® cells.

Expression of PD-L1 CAR in PD-L1 t-haNK cells were measured by flow cytometry and the results showed that more than 86.4% of cells from the PD-L1 t-haNK lines had stable CAR expression. FIG. 3.

Example 3: Cytotoxicity of PD-L1 t-haNK Cells on Target Cell Lines

Figure 4:
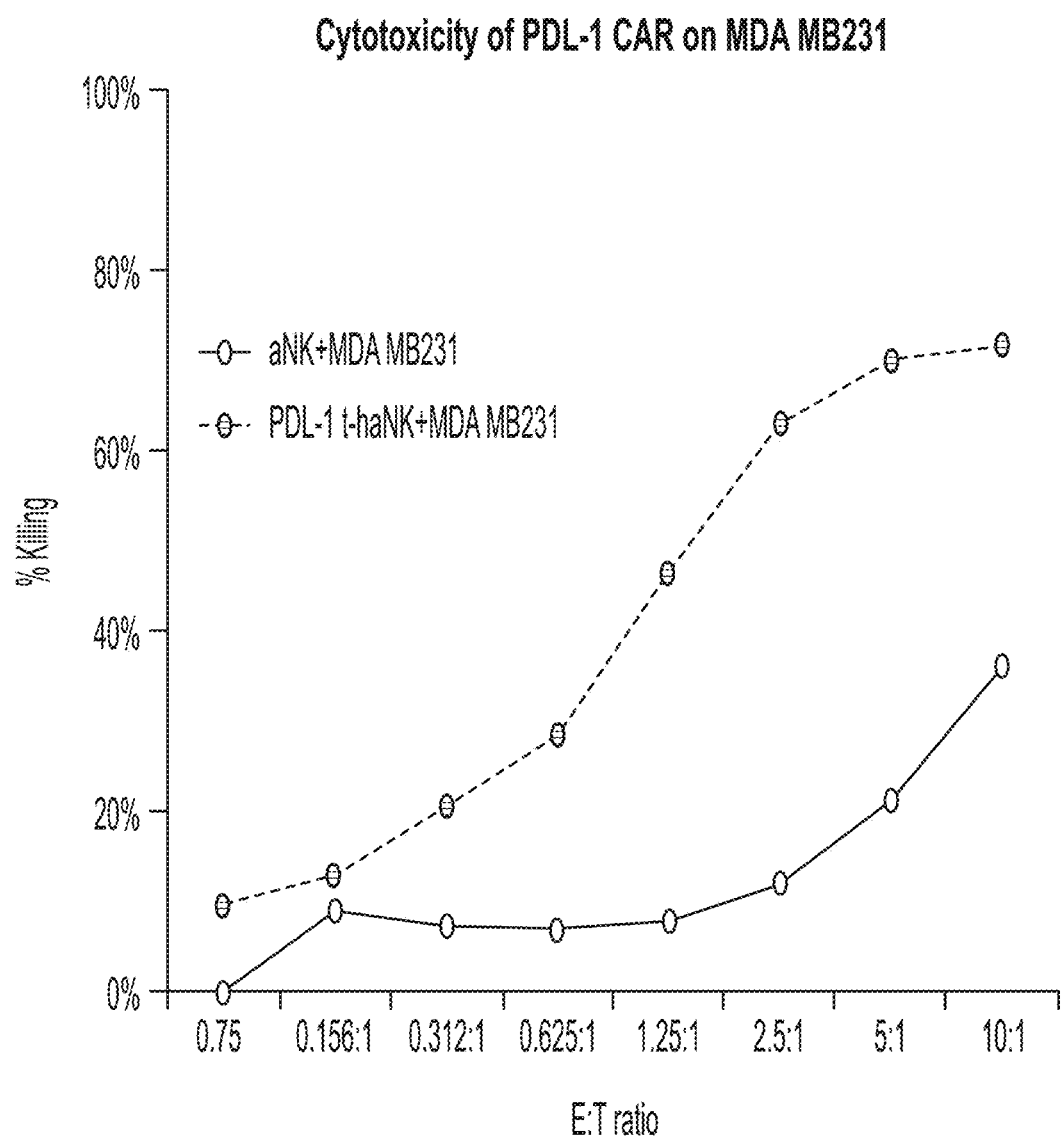
FIG. 4 shows the cytotoxic effect of PD-L1 t-haNK cells on MDA MB 231 cells. The parental aNK™ cells were used as control cells.

The cytotoxicity of t-haNK cells were analyzed by incubating with respective target cells. MDA-MB-231 cells, which express PD-L1, were used as target cells for PD-L1 t-haNK cells. The results show that the PD-L1 t-haNK cells effectively killed their respective target cells. See FIG. 4.

The cytotoxicity of PD-L1 t-haNK cells on MDSCs were also tested on MDSCs. MDSCs used in the experiments were generated form peripheral blood mononuclear cells (PBMCs) obtained from blood and separated on a Ficoll gradient. MDSCs were further enriched by positive magnetic selection for CD11b and expanded in numbers in culture media supplemented recombinant GM-CSF and IL-6 (Goedegebuure et al, 2011, Current Cancer Drug Targets, Vol. 11, issue 6, 2011). The MDSCs were then exposed at various effector to target ratios (E:T ratio) to the PD-L1 t-haNK cells.

Figure 5A:
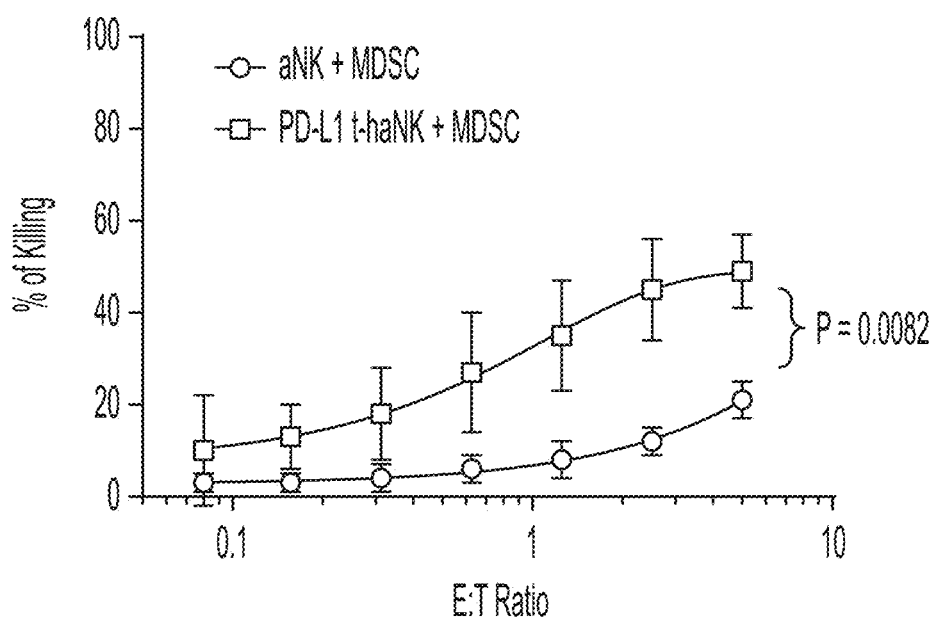
FIG. 5A shows the cytotoxic effect of PD-L1 t-haNK cells on myeloid-derived suppressor cells (MDSCs).

As shown in FIG. 5A, PD-L1 t-haNK cells effectively lysed (killed) the MDSCs. The cytotoxicity of the PD-L1-t-haNK cells was at least 50% higher than that of the parental aNK™ cells; a significantly higher percentage (at least 50% higher) of target cells were killed by either t-haNK cell lines. As the MDSCs are one of the main suppressor cells in the tumor microenvironment, this results show that these PD-L1 t-haNK cells can be used to effectively treat solid tumor. These results also suggest that PD-L1 t-haNK cells function by first eliminating MDSCs from tumor microenvironment through CAR mediated cytotoxicity, and then killing the tumor cells by t-haNK cells themselves or by other immune cells or specific tumor target therapy.

Figure 5C:
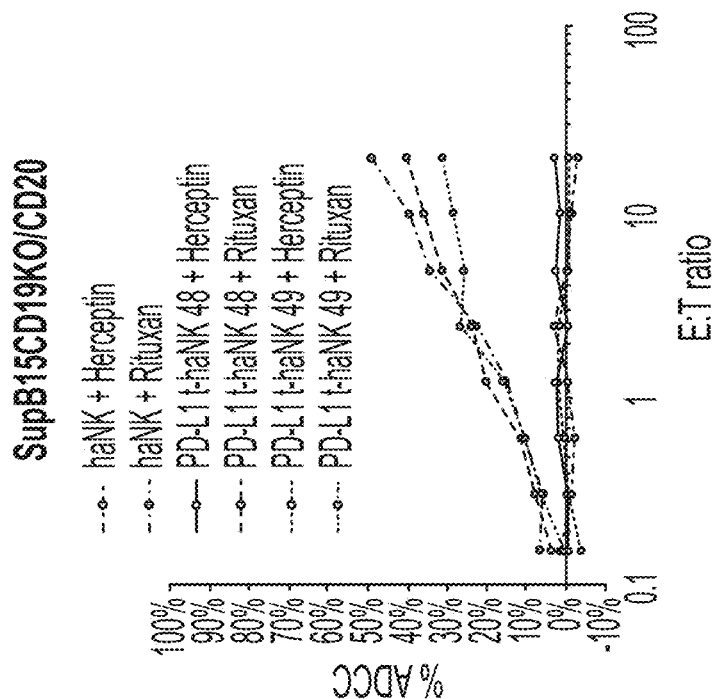
FIG. 5C shows the antibody-dependent cell-mediated cytotoxicity (ADCC) activity of PD-L1 t-haNK cells, when combined with the anti-CD20 antibody Rituximab, on engineered SUP-B15 cells. These engineered SUP-B15 cells express CD20 but not CD19. Herceptin was used as a control antibody.
Figure 5B:
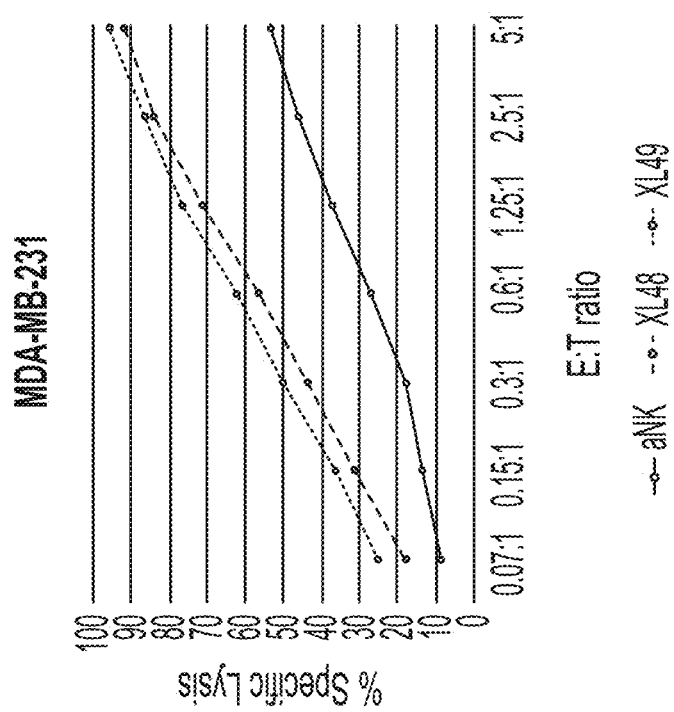
FIG. 5B shows the cytotoxic effect of PD-L1 t-haNK cells on aNK™-resistant, PD-L1-positive MDA-MB-231 cell line. XL-48 and XL-49 are two PD-L1 t-haNK populations expressing CARs comprising two different scFv domain derived from two different anti-PD-L1 antibodies.

FIG. 5B shows that PD-L1 t-haNK cells enhanced specific killing of the aNK™-resistant, PD-L1-positive MDA-MB-231 cell line. XL-48 and XL-49 are two PD-L1 t-haNK populations expressing CARs comprising two different scFv domain derived from two different anti-PD-L1 antibodies. FIG. 5C shows that PD-L1 t-haNK cells had antibody-dependent cell-mediated cytotoxicity (ADCC) activity against engineered SUP-B15 cells (CD19$^-$, CD20$^+$) when combined with the anti-CD20 antibody Rituximab, and the ADCC activity was comparable to that of haNK® cells expressing the CD16(158V) receptor only. The anti-Her2 antibody Herceptin was used in the experiments as a control antibody.

The inventors further investigated in several in vivo experiments the activity of PD-L1 t-haNK cells. More particularly, NSG mice (JAX), females, 9-10 weeks old, were used for the MDA-MB-231 model (24 animals using fresh cells) and HCC827 model (24 animals using fresh cells and 6 animals using cryopreserved cells). The MDA-MB-231 model was a human breast adenocarcinoma model, while the HCC827 was a human lung adenocarcinoma model. Mice were inoculated subcutaneous on both flanks and average tumor burden upon treatment initiation was 100 mm$^3$ (MDA-MB-231) and 75-80 mm$^3$ (HCC827). Anti-PDL1 t-haNK, freshly prepared, irradiated, were give at a concentration of 5E7 cells/mL, while anti-PDL1 t-haNK, cryopreserved, irradiated, were given at a concentration of 2E7 cells/mL. Vehicle control was growth medium alone. Administration was i.v. and intratumoral. Dosages for IV: Freshly prepared cells: 1E7 cells/dose in 200 µL, and cryopreserved cells: 4E6 cells/dose in 200 µL. Intratumoral dosing was at 2.5E6 cells/tumor/dose in 50 µL. Dosing frequency was twice a week for 4 consecutive weeks. First day of dosing was determined to be Day 1.

Figure 6B:
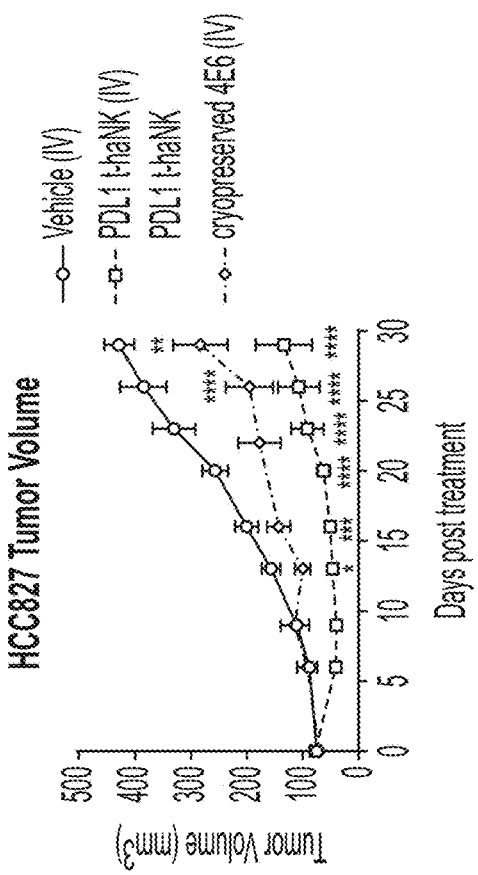
FIG. 6B shows in vivo tumor growth of HCC827 derived tumors in mice treated with vehicle and PD-L1 t-haNK cells using i.v. administration.
Figure 6A:
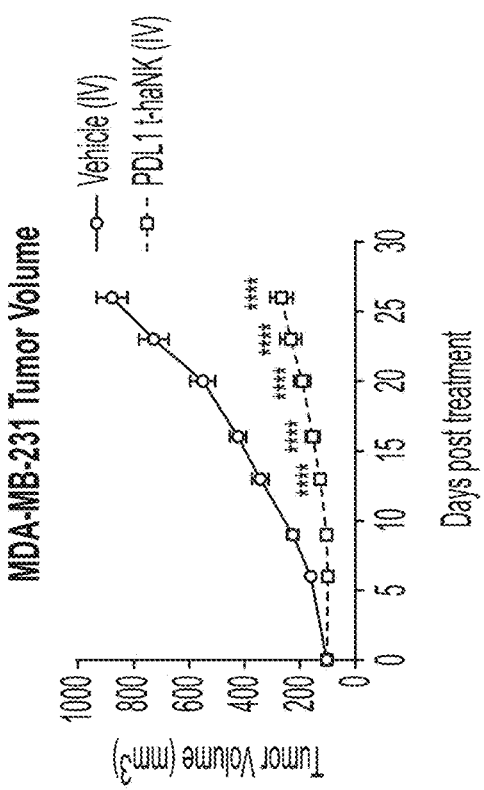
FIG. 6A shows in vivo tumor growth of MDA-MB-231 derived tumors in mice treated with vehicle and PD-L1 t-haNK cells.

Notably, as is shown in FIG. 6A and FIG. 6B, freshly prepared PD-L1 t-haNK cells (1E7 cells/dose) led to marked and long-lasting tumor growth inhibition in both MDA-MB-231 and HCC827 models when administered intravenously: Here, for MDA-MB-231 tumor stasis was observed with TGI on Day 16 was 84% (peak), and TGI on Day 26 was 79% (last measurement). For HCC827 tumor regression was observed with TGI on Day 16 at 120% (peak) and TGI on Day 29 at 84% (study end). Cryopreserved PD-L1 t-haNK cells (4E6 cells/dose) also showed statistically significant efficacy in suppressing tumor growth compared to vehicle control. Here, TGI on Day 26 was 60% (peak) and TGI on Day 29 was 40% (study end).

Moreover, freshly prepared PD-L1 t-haNK cells (1E7 cells/dose) also led to a significant reduction of metastatic disease burden in the MDA-MB-231 model as compared to vehicle. While 100% of all animals in the control developed metastatic disease, only 50% of the animals treated with the PD-L1 t-haNK cells developed metastases (all single organ findings). See Table below.

TABLE 3

PD-L1 t-haNK treatment reduced metastatic disease burden in multiple organs in MDA-MB-231 tumor-bearing mice

| Group | Animal | Macroscopic lesions found in: |
|---|---|---|
| A (vehicle) | 1 | Liver, lungs |
| | 2 | Ax LNs, liver, lungs |
| | 3 | Ax LN (left), liver, lungs |
| | 4 | Liver, lungs |
| | 5 | Ax LNs, spleen, liver, lungs |
| | 6 | Ax LNs, liver, lungs |
| B (PD-L1 t-haNK) | 1 | None |
| | 2 | Lungs |
| | 3 | Ax LNs |
| | 4 | None |
| | 5 | Ax LN (left) |
| | 6 | None |

Figure 7:
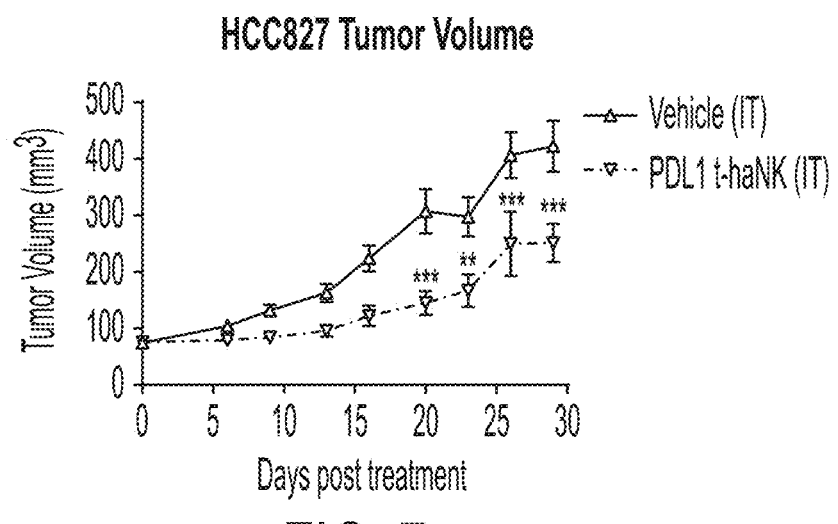
FIG. 7 shows in vivo tumor growth of HCC827 derived tumors in mice treated with vehicle and PD-L1 t-haNK cells using i.t. administration.

When administered intratumorally, significant tumor growth inhibition was also observed in the HCC827 model, but not in the MDA-MB-231 model. Here, the TGI for HCC827 was 70% on Day 20 (peak), and 49% on Day 29 (study end) as shown in FIG. 7.

Therefore, it should be noted that PDL1 t-haNK cells demonstrated remarkable efficacy in the two subcutaneous tumor models. Specifically, IV dosing of freshly prepared PD-L1 t-haNK cells at the dosing level of 1E7 cells/dose, twice a week for 4 weeks, showed marked anti-tumor efficacy in both of the subcutaneous xenograft models tested. The treatment resulted in tumor stasis in MDA-MB-231 tumor-bearing mice, with a peak TGI of 84% on Day 16 and an end-of-study TGI of 79% ($P<0.0001$ for both time points by 2-way ANOVA followed by multiple comparison by Tukey test), and tumor regression in the HCC827 model, with a peak TGI of 120% on Day 16 and an end-of-study TGI of 84% ($P<0.0001$). IV dosing of cryopreserved PD-L1 t-haNK cells at the dosing level of 4E6 cells/dose, twice a week for 4 weeks, also showed significant therapeutic efficacy in the HCC827 tumor model, reaching a peak TGI of 60% ($P<0.0001$), and an end-of-study TGI of 40% ($P<0.01$).

IT dosing of freshly prepared PD-L1 t-haNK cells at the dosing level of 2.5E6 cells/dose/tumor, twice a week for 4 weeks, effectively suppressed the growth of HCC827 tumors, resulting in a peak TGI of 70% on Day 20 and an end-of-study TGI of 49% ($P<0.001$). The MDA-MB-231 tumors, however, were not sensitive to PD-L1 t-haNK cells administered intratumorally.

Figure 8:
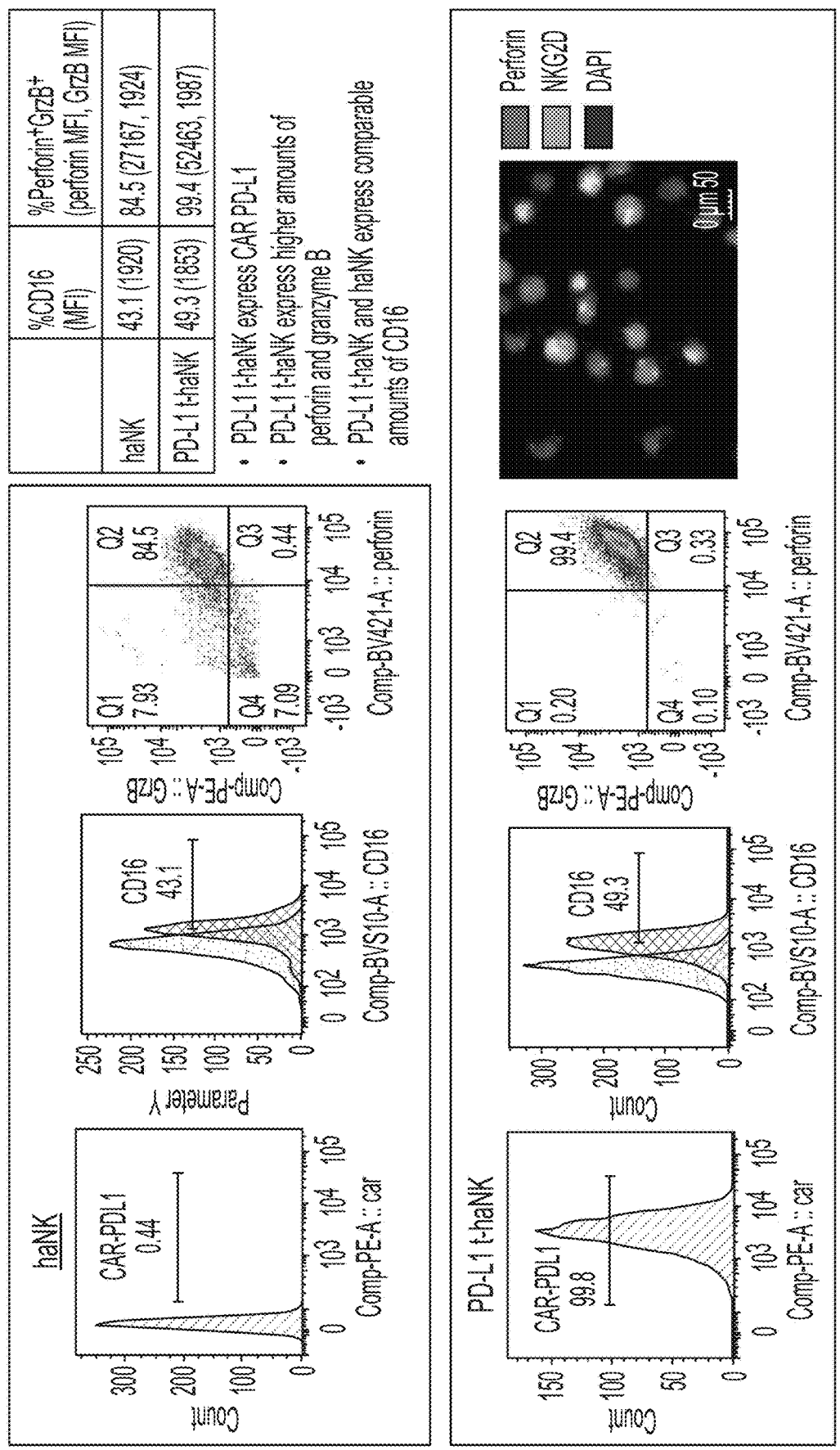
FIG. 8 shows exemplary differences between PD-L1 t-haNK cells and haNK cells.
Figure 9:
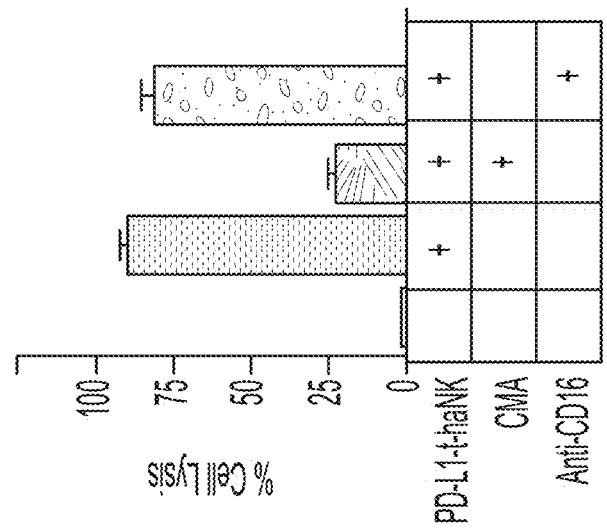
FIG. 9 shows exemplary data comparing cytotoxicity of PD-L1 t-haNK cells and haNK® cells against MDA-MB-231 cells.
Figure 9:
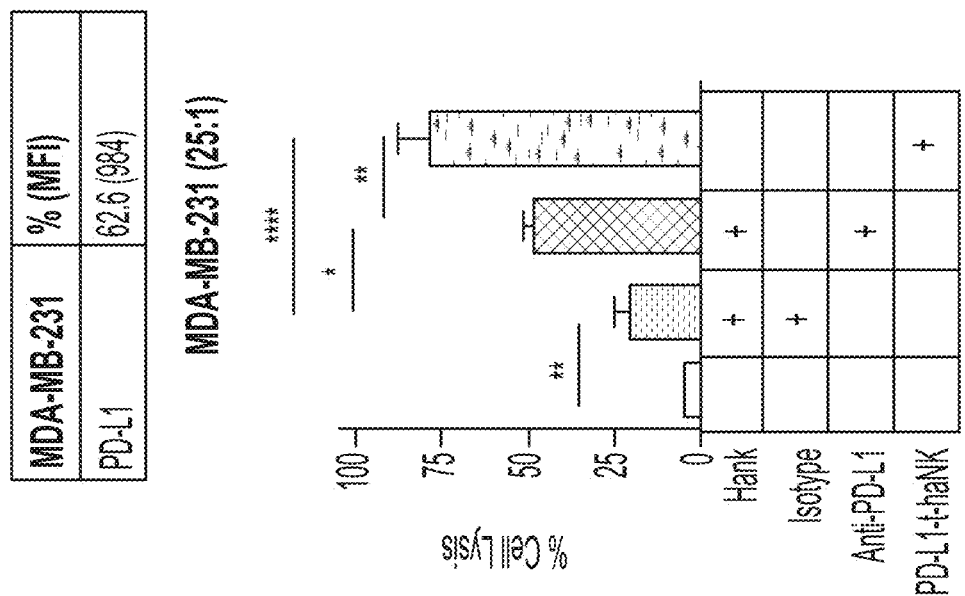

In still further experiments, the inventors compared expression of various markers in PD-L1 t-haNK cells versus haNK cells, and selected results are shown in FIG. 8. As is readily apparent, PD-L1 t-haNK cells expressed very high quantities of the PD-L1 CAR while also expressing substantial quantities of CD16. More notably, PD-L1 t-haNK cells had an increased expression in perforin and granzyme B, which is likely contributing to the enhanced cytotoxicity of the PD-L1 t-haNK cells as is shown in FIG. 9. Here, in the PD-L1high cell line (MDA-MB-231) PD-L1 t-haNK outperformed haNK, and anti-PD-L1 CAR-mediated killing by PD-L1 t-haNK outperformed anti-PD-L1 Ab mediated ADCC with haNK. Moreover, it was observed that killing was dependent on perforin/granzyme (killing activity significantly abrogated by concanamycin-a (perforin/granzyme inactivator)), and killing was not affected by anti-CD16.

Figure 10:
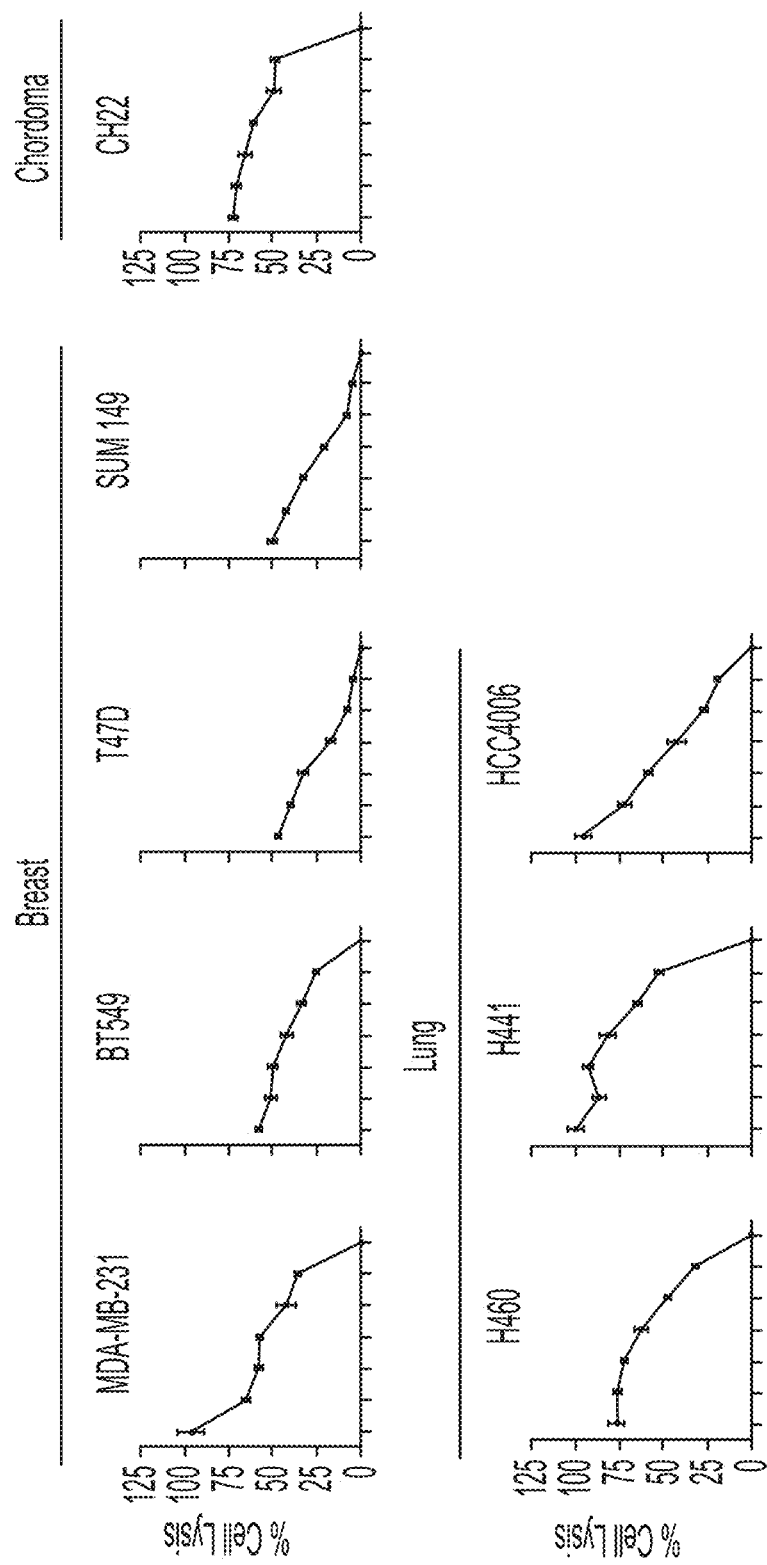
FIG. 10 shows exemplary data comparing cytotoxicity of PD-L1 t-haNK cells against various tumor cells.
Figure 10:
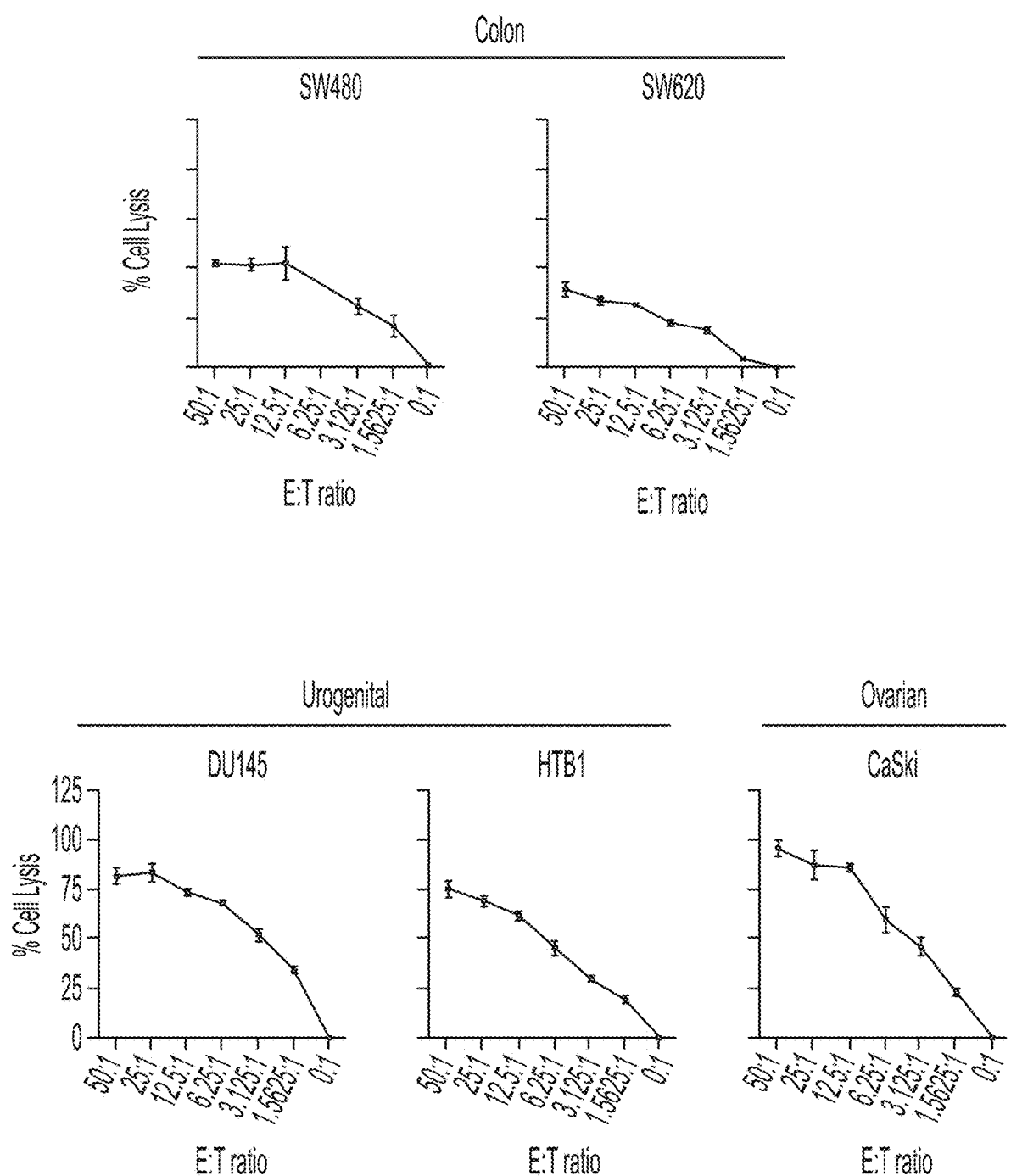

The inventors still further investigated if PD-L1 t-haNK cells were also cytotoxic against various tumor cells in vitro. FIG. 10 shows exemplary results where irradiated PD-L1 t-haNK were co-cultured with different tumors including breast (n=4), lung (n=3), colon (n=2), urogenital (n=2), chordoma and ovarian cell lines. Varying degrees of killing were observed for each cell line, with diminishing killing capacity observed as E:T ratio decreases. Notably, 13/13 cell lines were killed by PD-L1 t-haNK.

Figure 11:
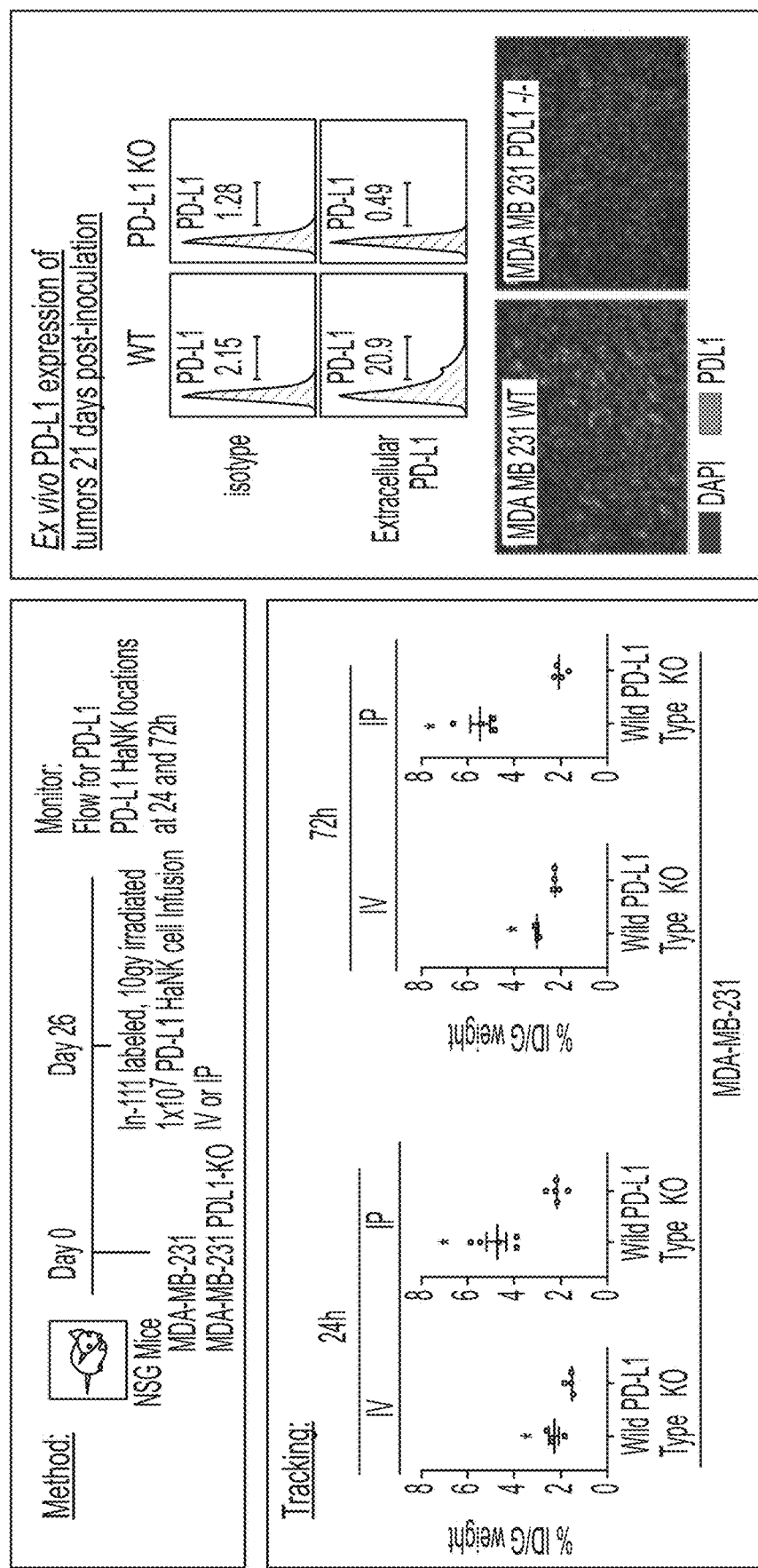
FIG. 11 shows exemplary data comparing tracking of PD-L1 t-haNK cells to tumors established from MDA-MB-231 cells and PD-L1 knock-out MDA-MB-231 cells.

In yet further experiments, the inventors investigated whether PD-L1 t-haNK cells would traffic into a tumor in vivo. As can be seen from the results in FIG. 11, PD-L1 t-haNK cells tracked to PD-L1 expressing MDA-MB-231 TNBC tumors (significant over PD-L1 null). Moreover, the IP route of administration of PD-L1 t-haNK cells mediated significantly greater levels of PD-L1 t-haNK cell accumulation than IV administered cells. Here, mice were inoculated with MDA-MB-231 cells and PD-L1 knock-out MDA-MB-231 cells. The flow of the PD-L1 t-haNK cells was monitored after 24 and 72 hours for both cell lines. Clearly, the PD-L1 t-haNK cell tracked to tumors with PD-L1 expression. Further results are shown after 21 days ex vivo where once more PD-L1 t-haNK cell tracked to tumors with PD-L1 expression.

Figure 12:
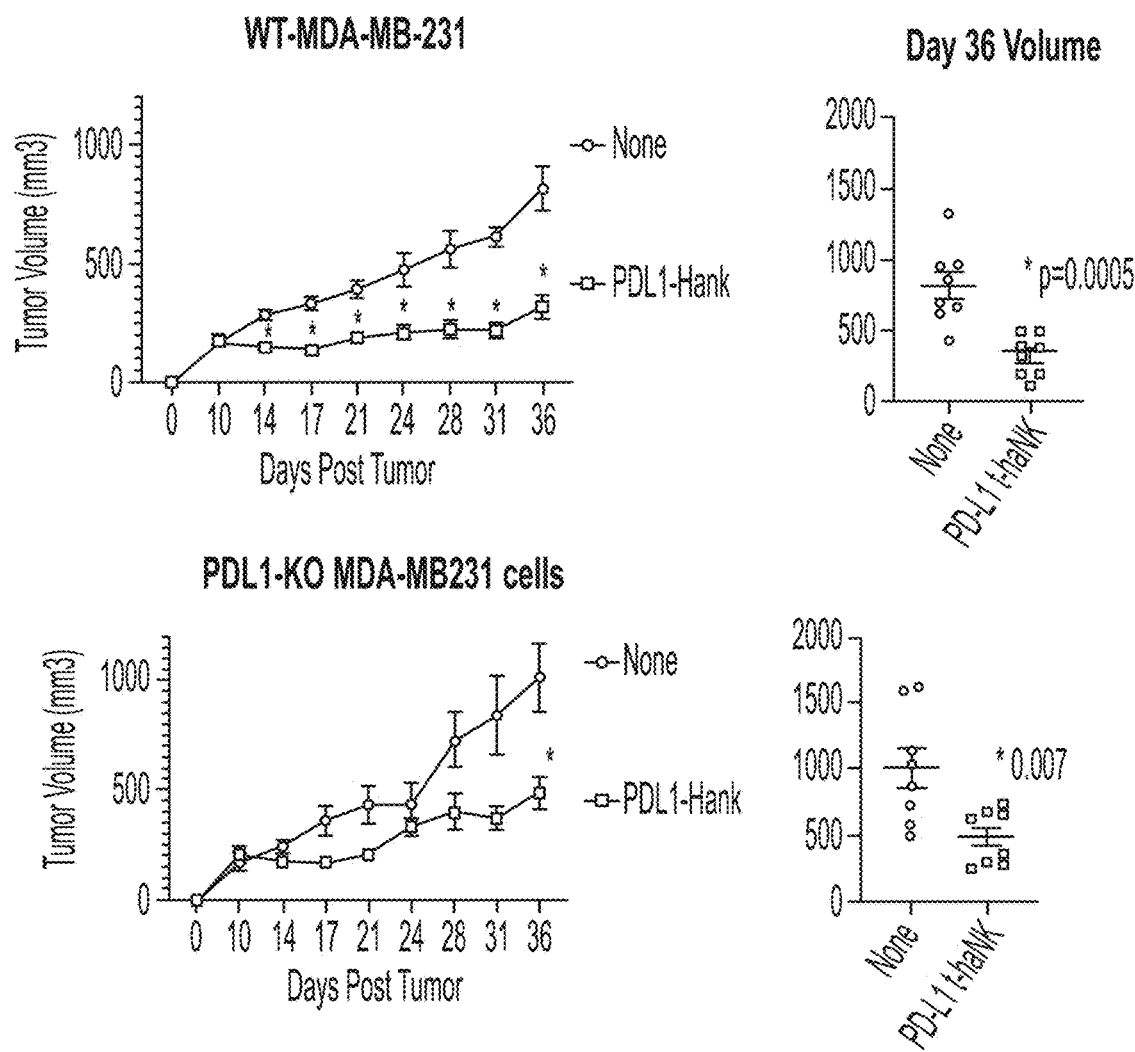
FIG. 12 shows exemplary data comparing tumor growth from MDA-MB-231 cells and PD-L1 knock-out MDA-MB-231 cells in animals treated with PD-L1 t-haNK cells.

Tumor growth curves were measured in vivo using the same model and exemplary results are shown in FIG. 12. Notably, PD-L1 t-haNK cells mediated significant antitumor activity of after only one injection, which was maintained. PD-L1 t-haNK cells also mediated significant antitumor activity on MDA-MB-231 PD-L1 KO cells (day 36).

Figure 13:
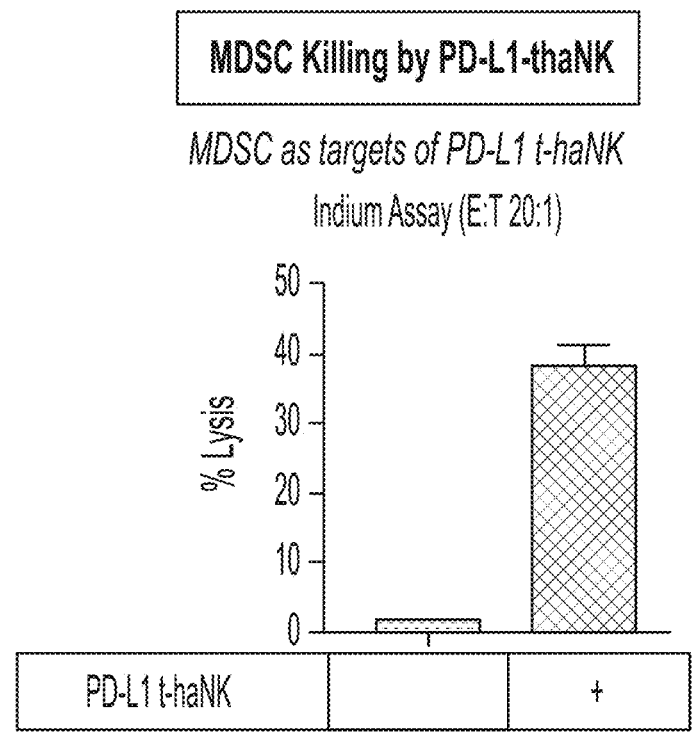
FIG. 13 shows exemplary data demonstrating cytotoxicity of PD-L1 t-haNK cells against MDSCs.

Human MDSCs were also tested for susceptibility to cytotoxicity PD-L1 t-haNK cells. To that end, PBMCs were cultured for 7 days in the presence of IL-1b, IL-6, PGE2, TGFb1, TNFa, VEGF, and GM-CSF, and expanded cells were selected using CD33 selection. Upon confirmation of the MDSC phenotype (CD11b+, HLA-DRneg, CD33), a functional cytotoxicity assay was performed, and exemplary results are shown in FIG. 13. As can be seen from the figure, MDSCs are also effectively killed by PD-L1 t-haNK cells. In this context, it should be noted that M2 macrophages are also deemed suitable targets for PD-L1 t-haNK cell mediated cell killing as M2 macrophages also express PD-L1 (see e.g., BMC Cancer (2015) 15:577 DOI 10.1186/s12885-015-1546-9).

What is claimed is:

1. A natural killer (NK)-92 cell having American Type Culture Collection (ATCC) deposit number CRL-2407 transfected to express a protein encoded by a recombinant construct comprising a nucleic acid molecule having the nucleotide sequence of SEQ ID NO:11 to thereby effect expression of an anti-programmed death-ligand 1 (PD-L1) chimeric antigen receptor (CAR), an endoplasmic reticulum interleukin-2 (erIL-2) and a fragment crystallizable (Fc) receptor, wherein the PD-L1 CAR comprises anti PD-L1 scFv, CD8 Hinge, CD28 transmembrane domain, and FcεRIγ signaling domain, and wherein the Fc receptor is CD16.

2. The NK-92 cell of claim 1, wherein NK-92 cell is capable of killing a PD-L1-expressing cell.

3. The NK-92 cell of claim 2, wherein the PD-L1-expressing cell is a myeloid-derived suppressor cell (MDSC), a tumor associated macrophage (TAM), or a tumor cell.

4. The NK-92 cell of claim 1, wherein direct cytotoxicity of the NK-92 cell on PD-L1-expressing cells is 40-100% when the effector to target ratio is 10.

5. The NK-92 cell of claim 1, wherein direct cytotoxicity of the NK-92 cell on PD-L1 expressing cells is higher than of a NK92 cell not transfected with the nucleic acid having the SEQ ID NO:11.

6. The NK-92 cell of claim 1, wherein an antibody-dependent cell-mediated cytotoxicity (ADCC) activity of the NK-92 cell is at 20%-60% when the effector to target ratio is 10.

7. A recombinant construct comprising a nucleic acid molecule having the nucleotide sequence of SEQ ID NO: 11.

8. A NK-92 cell having ATCC deposit no. CRL-2407, transfected with a recombinant construct having nucleotides 1552-4681 of SEQ ID NO:11, that encodes for a PD-L1 CAR, an erIL-2, and a Fc receptor, wherein the PD-L1 CAR comprises anti PD-L1 scFv, CD8 Hinge, CD28 transmembrane domain, and FcεRIγ signaling domain, and wherein the Fc receptor is CD16.

9. A NK-92 cell having ATCC deposit no. CRL-2407, and expressing from a recombinant construct comprising a nucleic acid molecule a PD-L1 CAR having at least 90% sequence identity to amino acids 1-272 of SEQ ID NO:12, an erIL-2 having at least 90% sequence identity to SEQ ID NO:13, and a Fc receptor having at least 90% identity to amino acids 428-681 of SEQ ID NO:12, wherein the PD-L1 CAR comprises anti PD-L1 scFv, CD8 Hinge, CD28 transmembrane domain, and FcεRIγ signaling domain, and wherein the Fc receptor is CD16, and wherein direct cytotoxicity of the NK-92 cell on PD-LI-expressing cells is 40-100% when the effector to target ratio is 10.

* * * * *